(12) United States Patent
Schindler et al.

(10) Patent No.: US 8,334,121 B2
(45) Date of Patent: Dec. 18, 2012

(54) METHOD OF CONVERTING CELLULOSIC BIOMASS TO ALCOHOL USING WEB COMPRISING FINE FIBER AND BIOACTIVE PARTICULATE

(75) Inventors: Melvin S. Schindler, Piscataway, NJ (US); Veli Engin Kalayci, Farmington, MN (US); Mark A. Gogins, Roseville, MN (US)

(73) Assignee: Donaldson Company, Inc., Minneapolis, MN (US)

( * ) Notice: Subject to any disclaimer, the term of this patent is extended or adjusted under 35 U.S.C. 154(b) by 970 days.

(21) Appl. No.: 12/279,031

(22) PCT Filed: Feb. 13, 2007

(86) PCT No.: PCT/US2007/004043
§ 371 (c)(1),
(2), (4) Date: Feb. 19, 2009

(87) PCT Pub. No.: WO2007/095335
PCT Pub. Date: Aug. 23, 2007

(65) Prior Publication Data
US 2009/0221047 A1 Sep. 3, 2009

Related U.S. Application Data

(60) Provisional application No. 60/773,067, filed on Feb. 13, 2006.

(51) Int. Cl.
*C12P 7/16* (2006.01)
*C12P 7/06* (2006.01)
*C12N 9/00* (2006.01)
*C12N 1/20* (2006.01)
*C12N 15/00* (2006.01)
*C07H 21/04* (2006.01)

(52) U.S. Cl. ..... 435/160; 435/161; 435/183; 435/252.3; 435/320.1; 536/23.2

(58) Field of Classification Search ........................ None
See application file for complete search history.

(56) References Cited

U.S. PATENT DOCUMENTS

| | | |
|---|---|---|
| 3,019,127 A | 1/1962 | Czerwonka et al. |
| 4,753,730 A | 6/1988 | Maurer |
| 5,554,520 A | 9/1996 | Fowler et al. |
| 5,595,893 A | 1/1997 | Pometto, III et al. |
| 5,755,967 A | 5/1998 | Meagher et al. |
| 5,965,091 A | 10/1999 | Navarre |
| 7,704,740 B2 | 4/2010 | Schindler et al. |
| 2002/0164731 A1 | 11/2002 | Eroma et al. |
| 2004/0037813 A1* | 2/2004 | Simpson et al. ............. 424/93.7 |
| 2005/0058842 A1 | 3/2005 | Liebmann-Vinson et al. |
| 2006/0008885 A1 | 1/2006 | Wahnon et al. |

FOREIGN PATENT DOCUMENTS

| | | |
|---|---|---|
| GB | 2 230 278 | 10/1990 |
| WO | WO 03/013732 | 2/2003 |

OTHER PUBLICATIONS

Sedlak et al. Appl Biochem Biotechnol. 2004 Spring;113-116:403-16.*
Li et al. J. Biomed. Mater. Res., vol. 60, pp. 613-621 (2002).*
Ito et al. Biotechnol Prog. May-Jun. 2004, 20(3):688-91.*
Kunduru et al., "Continuous ethanol production by Zymomonas mobilis and Saccharomyces cerevisiae in biofilm reactors", J. Ind. Microbiol. Apr. 16, 1996 (4): 249-56, Abstract only from PubMed.
Shukla et al., "Acetone-Butanol-Ethanol (ABE) Production in a Novel Hollow Fiber Fermentor-Extractor" , Biotechnology and Bioengineering, vol. 34, pp. 1158-1166 (1989).
Mori et al., "Ethanol Production from Starch in a Pervaporation Membrane Bioreactor Using *Clostridium thermohydrosulfuricum*", Biotechnology and Bioengineering, vol. 36, pp. 849-853 (1990).
Demain et al., "Cellulase, Clostridia, and Ethanol", Microbiology and Molecular Biology Reviews, Mar. 2005, pp. 124-154.
Ezeji et al., "Acetone butanol ethanol (ABE) production from concentrated substrate: reduction in substrate inhibition by fed-batch technique and product inhibition by gas stripping", Appl. Microbiol. Biotechnol. (2004) 63: 653-658.
Herrero et al., "Development of Ethanol Tolerance in *Clostridium thermocellum:* Effect of Growth Temperature", Applied and Environmental Microbiology, Sep. 1980, pp. 571-577.
Lynd et al., "Consolidated bioprocessing of cellulosic biomass: an update", Current Opinion in Biotechnology 2005, 16: 577-583.
Qureshi et al., "Biofilm reactors for industrial bioconversion processes: employing potential of enhanced reaction rates", Microbial Cell Factories 2005, 4:24.
Ribeiro et al., "Influence of the carbon source on the anaerobic biomass adhesion on polyurethane foam matrices", Journal of Environmental Management 74 (2005) pp. 187-194.
Shoham et al., "The cellulosome concept as an efficient microbial strategy for the degradation of insoluble polysaccharides", Trends in Microbiology, vol. 7, No. 7, Jul. 1999, pp. 275-281.
Warnick et al., "*Clostridium phytofermentans* sp. Nov., a cellulolytic mesophile from forest soil", International Journal of Systematic and Evolutionary Microbiology (2002), 52, pp. 1155-1160.
Yang et al., "Kinetics and Stability of GM-CSF Production by Recombinant Yeast Cells Immobolized in a Fibrous-Bed Bioreactor", Biotechnol. Prog. 1996, 12, pp. 449-456.
Lin et al., "Ethanol fermentation from biomass resources: current state and prospects", Appl. Microbiol. Biotechnol. (2006) 69: 627-642.
Lynd et al., "Microbial Cellulose Utilization: Fundamentals and Biotechnology", Microbiology and Molecular Biology Reviews, Sep. 2002, pp. 506-577.

(Continued)

*Primary Examiner* — Christian Fronda
(74) *Attorney, Agent, or Firm* — Merchant & Gould P.C.

(57) ABSTRACT

The assemblies of the invention can comprise a fine fiber layer forming a multilamellar web or matrix, having dispersed within the fine fiber layer a bioactive particulate material, including cells, enzymes or microorganisms. Fluid that flows through the assemblies of the invention can have any material dispersed or dissolved in the fluid react with, be absorbed by, or adsorbed onto, the bioactive particulate within the nanofiber layer. The assemblies of the invention can be used to treat or purify fluid streams. The assemblies of the invention can be used in conjunction with a bioreactor system, a bioartificial organ, or a culture container.

17 Claims, No Drawings

OTHER PUBLICATIONS

Tomme et al., "Characterization and affinity applications of cellulose-binding domains", Journal of Chromatography B, 715 (1998) pp. 283-296.

Yang ST et al., "A fibruous-bed bioreactor for continuous production of monoclonal antibody by hybridoma.", Adv Biochem Eng Biotechnol., 2004; 87: 61-96, Abstract only from PubMed.

Leschine, "Fuels from Biomass: Microbially Mediated Production of Cellulosic Ethanol", UMass Amherst: Advanced Energy Research, http://www.umass.edu/research/energy/harvest.html, 1 page, (2007).

Boraston et al., "Carbohydrate-binding modules: fine-tuning polysaccharide recognition", Biochem. J. (2004) 382: 769-781.

Tan et al., "Characterization of bulk properties of nanofibrous scaffolds from nanomechanical properties of single nanofibers", J. Biomed Mater Res 77A: 526-533, 2006.

Ebert, "The Holy Grail of Consolidated Bioprocessing", Ethanol Producer Magazine, Nov. 2007, http://www.ethanolproducer.com/articles/3422/the-holy-grail-of-consolidated-bioprocessing, 2 pages.

* cited by examiner

US 8,334,121 B2

METHOD OF CONVERTING CELLULOSIC BIOMASS TO ALCOHOL USING WEB COMPRISING FINE FIBER AND BIOACTIVE PARTICULATE

This application is being filed on 8 Aug. 2008 as a US National Stage of PCT International Patent Application No. PCT/US2007/004043, filed 13 Feb. 2007 in the name of Donaldson Company, Inc., a U.S. national corporation, applicant for the designation of all countries except the U.S., and Melvin S. Schindler and Mark A. Gogins, both citizens of the U.S., and Veli Kalayci, a citizen of Turkey, applicants for the designation of the U.S. only, and claims priority to U.S. Provisional Patent Application Ser. No. 60/773,067, filed Feb. 13, 2006.

BACKGROUND OF THE INVENTION

Polymer webs can be made by extrusion, melt spinning, air laid and wet laid processing, etc. Polymer webs have been shown to be a useful substrate for cell culture and tissue culture applications. See, for example, U.S. 20050095695 and WO2006/094076. Bioreactors currently provide an efficient means to produce industrial chemicals, treat and detoxify wastewater, and produce high value pharmaceuticals, biologicals, and small molecules. Bioreactors are generally categorized into four different types (stirred-tank, airlift, hollow-fiber and fixed bed) and can be operated in batch or continuous modes. Isolated enzymes, catalytic molecules (organic and inorganic), microorganisms, animal cells, or plant cells are normally employed as the functional agents within the bioreactor. The cells or microorganisms are typically cultured in suspension or immobilized on a surface or particle. Cell proliferation, cell density, culture stability, scale up potential, and product yield is highest while cell damage resulting from shear stress is lowest when the cells or microorganisms are immobilized to a surface. Similar operating advantages exist when purified enzymes are tethered to surfaces in a bioreactor. The amount of enzyme required is reduced while the stability of the enzyme and product formation is increased when compared to enzyme activity in solution. In addition, immobilization of the culture/enzyme significantly improves the time and cost of the product separation process.

Given the aforementioned considerations, the most important variable for maximizing the output and reaction rates of a bioreactor under optimized parameters is the mass of productive cells or microorganisms (for culture based bioreactors) or the amount of functional enzyme (for enzyme based bioreactors). These considerations led to the development of fibrous matrices having 3-dimensional structure, high surface to volume ratio, high void space, and low pressure drop, and high mass-transfer efficiency. While currently available fibrillar and hollow-fiber reactors have obtained certain levels of efficiency and performance compared to standard fixed bed reactors, a substantial need remains in the industry for a fibrillar reactor having improved density of catalytic and attachment surfaces within an equivalent reactor footprint.

SUMMARY OF THE INVENTION

The web, substrate, or structure of the invention can comprise a substantially continuous fine fiber or nanofiber layered to form a multilamellar matrix containing the particulate of the invention. A bioactive, reactive, absorptive, or adsorptive fiber spacer or separation means in the form of a particulate can be combined with, or otherwise dispersed in, the fiber mass. The web of the invention includes a fiber web or layer and a fiber separation means or fiber spacer means adhered to the fiber that can be used in the form of a bioactive, reactive, absorbent, or adsorbent structure.

In certain embodiments, the web, substrate or structure of the invention is used as a growth media for a bioreactor. The fine fiber or nanofiber layer comprises a non-cytotoxic, non-biodegradable or biodegradable polymer, and a bioactive particulate that comprises a cell, microorganism, enzyme, bioactive molecule, or mixtures thereof. In aspects, the bioreactor of the invention can be used for filtration or purification of fluid streams, including wastewater streams. In other aspects, the bioreactor of the invention is used bioconversion of cellulose to ethanol, for biofilm formation in wastewater treatment, or for bioprocessing of cellulosic biomass, or for production of high value pharmaceuticals, antibodies, or small molecules, such as antibodies or recombinant polypeptides having a therapeutic activity.

In other embodiments, the web, substrate or structure of the invention can be used as a culture container. In aspects, the fine fiber layer and/or the particulate layer act as a substrate for the proliferation and differentiation of cells. In still other embodiments, the web, substrate or structure of the invention can be used as a bioartificial organ.

DETAILED DISCUSSION OF THE INVENTION

The invention relates to polymeric compositions in the form of fine fiber such as microfibers, nanofibers, in the form of fiber webs, or fibrous mats used with a particulate. The fiber web or fibrous mat can be formed into a high-density multilamellar stack or matrix. In some embodiments, the web of the invention comprises a substantially continuous fiber or nanofiber phase and dispersed in the fiber mass, a fiber separation means. In the various aspects of the invention, the fiber separation means can comprise a particulate phase in the web. The particulate can be found on the surface of the web, in surface products or throughout void spaces formed within the web. The fibrous phase of the web can be formed in a substantially singular continuous layer, can be contained in a variety of separate definable layers or can be formed into an amorphous mass of fiber having particulate inclusion phases throughout the web randomly forming inclusion spaces around the particulate and internal web surfaces.

The term "fine fiber" indicates a fiber having a fiber size or diameter of 0.001 to less than 5 microns or about 0.001 to less than 2 microns and, in some instances, 0.001 to 0.5 micron diameter. A variety of methods can be utilized for the manufacture of fine fiber. Chung et al., U.S. Pat. No. 6,743,273; Kahlbaugh et al., U.S. Pat. No. 5,423,892; McLead, U.S. Pat. No. 3,878,014; Barris, U.S. Pat. No. 4,650,506; Prentice, U.S. Pat. No. 3,676,242; Lohkamp et al., U.S. Pat. No. 3,841,953; and Butin et al., U.S. Pat. No. 3,849,241; U.S. Patent Publication No. 20050095695, and WO06/094076, all of which are incorporated by reference herein, disclose a variety of fine fiber technologies. The fine fiber of the invention is typically electrospun onto a substrate. The substrate can be a pervious or impervious material. In filtration applications, non-woven filter media can be used as a substrate. In other applications the fiber can be spun onto an impervious layer and can be removed for down stream processing. In such an application, the fiber can be spun onto a metal drum or foil. The substrate can comprise an expanded PTFE layer or Teflon® layer. Such layers are useful in a variety of applications that can provide both filtration and activity from the active particulate. In an embodiment, the substrate comprises a film. The film can be water soluble or water insoluble, biodegradable or biodissolvable. In an embodiment, the film is non-cytotoxic. In an embodiment, the film comprises polyvinyl alcohol, polychlorotrifluoroethylene, polystyrene, polymethylpentene, or polycyclo-olefin.

For the purpose of this invention, the term "media" includes a structure comprising a web comprising a substantially continuous fine fiber mass and the particulate or spacer means of the invention dispersed in the fiber. In this disclosure the term "media" indicates the web of the invention, comprising the fine fiber and dispersed particulate in combination with a substrate of some active or inert type disclosed herein. The term "growth media" or "culture media" includes a structure comprising a multilamellar stack or matrix comprising a substantially continuous fiber mass that can act as a growth surface, i.e. a synthetic surface that supports growth of cells or tissue. Bioactive particulate is dispersed in the multilamellar matrix.

The term "element" indicates the combination of the "media" or "growth media" of the invention with another component including cartridge components in the form of (e.g.) cylinder or flat panel structures. In this disclosure, the term "web" includes a substantially continuous or contiguous fine fiber phase. In an embodiment, the web comprises a spacer particulate phase. For filtration and purification applications, a continuous web is necessary to impose a barrier to the passage of a particulate contaminant loading in a mobile phase. A single web, two webs or multiple webs can be combined to make up the multilamellar stack or matrix of the invention.

In many applications, especially those involving relatively high flow rates, an alternative type of filter media, sometimes generally referred to as "depth" media, is used. A typical depth media comprises a relatively thick tangle of fibrous material. Depth media is generally defined in terms of its porosity, density or percent solids content. For example, a 2-3% solidity media would be a depth media mat of fibers arranged such that approximately 2-3% of the overall volume comprises fibrous materials (solids), the remainder being air or gas space.

The web can be spun in such a way to disperse the active particulate or active separation means into the fiber. A preferred active particulate or spacer means comprises a bioactive, absorptive or adsorptive particulate. Such particulate can be dispersed within the polymer containing solution, or the particulate can be a gel phase in a composite comprising the fiber web. Where the fiber web or nanofibrillar network is part of a growth media in a bioreactor system, the particulate comprises a bioactive particulate. Bioactive particulates can be added to the multilamellar matrix either by inoculation, or by dispersal within the fiber web or nanofibrillar network. The particulate can be added to the web during formation or can be added after formation. Such a web, when electrospun, is characterized by a mass of interconnected nanofiber or fine fiber with the active separation or spacer means or particulate dispersed within the fiber web on the surface of the fiber web. Within the fiber web, the spacer particulate creates void spaces within the interconnected fibrous structure that reduces solidity and increases mobile fluid flow. The invention also comprises a web formed by forming a fine fiber mass with the simultaneous addition or a post spinning addition of the spacer particulate to the fiber layer. In such an embodiment, the particulate is interspersed throughout the mass of fibrous material. Lastly, the invention involves forming the spun layer in a complete finished web or thickness and then adding the active particulate to the surface of the web prior to incorporating the web into a useful article. Subsequent processing including lamination, calendaring, compression or other processes can incorporate the particulate into and through the fiber web. One advantage of either simultaneous addition of the particulate to the web as it is formed or to the web after formation, is obtained when the particulate is a solvent soluble particulate. Dissolving the soluble particulate in the solution would result in the incorporation of the material into the fiber without maintaining the particulate as a separate phase in the web. Adding the particulate to the web after formation preserves the solvent soluble material in its particulate form.

The web of the material can also have a gradient structure. In this disclosure, the term "gradient" indicates that some component (density, solidity, fiber size, etc.) of the web varies from one surface of the web to the opposite surface of the web. The gradient can be characterized by a variation in amount of active particulate, varying proportions of active and inert particulate, or other variation in particulate. The gradient can also be characterized in terms of a variation in the weight or the number of fibers. The gradient is formed by forming successively more or less fibers or more or less particulates within the web as the web is formed. Further, the concentration of spacer means or particulate can have a gradient aspect in which the size, weight or number of particulate materials per volume is substantially increased or reduced from one surface of the web to the other. In an embodiment, the media of the invention can be used in the form of a single fine fiber web or a series of fine fiber webs in a filter structure.

One aspect of the invention provides a web comprising a fibrous structure with a substantially continuous fine fiber network layer and a bioactive particulate, or a fiber network that comprises a bioactive substrate. The fine fiber can be a nanofiber. A nanofiber network can have a thickness of about the diameter of a single nanofiber or greater. In an embodiment, the network of one or more nanofibers defines the fibrous structure. The term "network" as used herein means a random or oriented distribution of nanofibers in space that is controlled to form an interconnecting net with spacing between fibers selected to preferentially enhance activation of a cell or tissue. The network has small spaces between the fibers that form pores or channels in the network. In an embodiment, interfiber spacing comprises from about 20 nm to about 2000 nm, from about 100 nm, to about 1500 nm, from about 100 nm to about 1000 nm, from about 100 nm to about 800 nm, from about 100 nm to about 600 nm, or from about 50 nm to about 600 nm. Preferably the pore size allows cells to penetrate and/or migrate through the single layer nanofiber network. Different pore or channel sizes are useful for different applications. In an embodiment, the pores or channels can have a diameter of about 20 nm to about 1000 nm, about 20 nm to about 2000 nm, about 0.01 to about 10 microns, about 0.01 to about 25 microns, or about 2 to about 10 microns.

A network can comprise a single layer of nanofibers, a single layer formed by a continuous nanofiber, multiple layers of nanofibers, multiple layers formed by a continuous nanofiber, or mat. The network can be unwoven or net. A network can have a thickness of about the diameter of a single nanofiber to about 250 µm. Physical properties of the network including, but not limited to, texture such as surface roughness, peak height, peak depth, total roughness, spacing between peaks, or peak count, elongation, rugosity, adhesivity, porosity, solidity, elasticity, geometry, interconnectivity, surface to volume ratio, fiber diameter, fiber solubility/insolubility, hydrophilicity/hydrophobicity, fibril density, and fiber orientation can be engineered to desired parameters using known methods.

In an embodiment, the nanofiber network comprises a thickness less than about 250 µm. In an embodiment, the thickness comprises about 150 µm to about 250 µm. In an embodiment, the thickness comprises about 50 µm to about 100 µm. In an embodiment, the thickness comprises about 10 µm to about 50 µm. In an embodiment, the thickness comprises about 5 µm to about 10 µm. In an embodiment, the thickness comprises about 30 nm to about 5000 nm. In an embodiment, the thickness comprises about 3000 nm to about 5000 nm. In an embodiment, the thickness comprises about 1000 nm to about 2000 nm. In an embodiment, the thickness comprises about 1000 nm to about 1500 nm. In an embodiment, the thickness comprises about 30 nm to about 2000 nm. In an embodiment, the thickness comprises about 100 nm to about 1000 nm. In an embodiment, the thickness comprises about 500 nm to about 1500 nm.

Physical properties of the growth substrate such as adhesivity, porosity, solidity, elasticity, geometry, interconnectivity, surface to volume ratio, solubility/insolubility, hydrophilicity/hydrophobicity, and density can be engineered to desired parameters. For example, the physical and geometric properties of the nanotopography of the nanofibrillar surface can be engineered to mimic the nanotopography of extracellular matrix (ECM) or basement membrane BM. In an embodiment, the nanofiber network comprises elongation of about 100 percent to about 500 percent. In an embodiment, the tensile modulus of the nanofiber network is less than about 300 MPa. In an embodiment, the tensile modulus is less than about 200 MPa. In an embodiment, the tensile modulus is less than about 100 MPa. In an embodiment, the tensile modulus is less than about 50 MPa. In an embodiment, the tensile modulus is less than about 10 MPa. In an embodiment, the tensile modulus is about 10 to 200 MPa, about 10 to 100 MPa, about 10 to 50 MPa, or about 2 to 10 MPa. Additionally, nano- and micro-environments that promote cellular activity of a particular cell or tissue can be constructed by layering growth surfaces that have selected physical and/or chemical properties. In an embodiment, the nanofiber network comprises a fiber diameter of about 30 nm to about 1200 nm, average interfiber spacing of about 100 nm to about 2000 nm, and solidity of about 70% or less.

The fibrous structure can include one or more fiber networks layered to form a multi-lamellar matrix. In an embodiment, the multi-lamellar matrix comprises a spacer. The spacer can function as a support structure, or substrate. The spacer provides sufficient openings to permit cells to penetrate and attach to the nanofiber network layers. The spacer can be water soluble or water insoluble, porous or non-porous, biodegradable or biodissolvable. Preferably the spacer is biocompatible. Bioactive molecules can be absorbed, adsorbed, attached, bound, or tethered to the spacer as described herein. The fine fiber can comprise a microfiber or other fine fiber, or an active or inert particulate, as described herein. The microfiber can be unwoven or net.

The bioactive particulate can be dispersed within the fiber phase. By dispersed, it is meant that the bioactive particulate is adhered to the fiber, attached to the fiber, bound to the fiber, tethered to the fiber, held within a void space within the web, or in a pocket penetrating partially in the web creating a space in the web surface. The web can be used as a growth surface, culture surface, catalytic surface, or attachment surface in bioreactor applications, including bioprocessing and bioconversion applications, or as a media for filter applications such as affinity chromatography, or wastewater treatment or purification applications. For high density multilamellar stacks or matrices for use in a bioreactor system, the thickness of each layer, the distance between the layers, and the porosity of the fiber surfaces can be adjusted to meet the requirements of a specific application, cell, microorganism, enzyme, or other bioactive molecule. In an embodiment, the thickness of each layer comprises about 0.25 to about 1.0 microns, the distance between the layers comprises about 1.0 to 2.0 microns, and the average pore size comprises about 0.2 to about 1.0 micron.

The bioactive particulate can be a cell, microorganism, enzyme, or other bioactive molecule. The cell can be an animal cell, plant cell, insect cell, bacterial cell, yeast cell, or fungal cell. Animal cells useful in the system and methods of the invention include stem cells, somatic cells, committed stem cells, differentiated cells, or tumor cells. The cells can be mouse or human. Examples of cells useful in the system and methods of the invention include, but are not limited to, osteoblasts, myoblasts, neurons, fibroblasts, glioblasts, germ cells, stem cells, hepatocytes, chondrocytes, keratinocytes, smooth muscle cells, cardiac muscle cells, connective tissue cells, glial cells, epithelial cells, endothelial cells, hormone-secreting cells, neurons, and lymphoid cells such as B cells, T cells, macrophages, and neutrophils. In an embodiment, the cells are CHO cells Examples of stem cells include, but are not limited to, embryonic stem cells, mesenchymal stem cells, bone marrow stem cells, amniotic and umbilical cord stem cells. The stem cells can be mammalian stem cells. In an embodiment, the stem cells are human or murine stem cells. In an embodiment, the stem cells are embryonic stem cells.

Examples of insect cells include, without limitation, cell lines such as *Drosophila* S2, *Spodoptera* Sf9 and Sf21, *Trichoplusia* Tn5, cells from *Bombyx mori* (silkworm), and cells from *Malacosoma disstria* (caterpillar), etc.

Examples of plant cells include, but are not limited to, parenchyma cells, collenchyma cells, sclerenchyma cells, xylem cells (i.e. water-conducting cells), phloem cells, root cells, root hair cells, leaf cells, palisade cells, guard cells, and callus cells, etc.

Examples of bacterial cells include, but are not limited to, Gram-positive bacteria such as Actinobacteria, Firmicutes (species of *Clostridium, Streptococcus, Staphylococcus, Bacillus, Corynebacterium, Listeria*), etc., Gram-negative bacteria such as species of *Neisseria, Branhamella, Vibrio, Spirochetes, Enterobacter* (including *E. coli*, and *Proteus*), *Pseudomonas*, etc., cells from species such as *Deinococcus-Thermus, Salmonella, Shigella, Serratia*, and *Campylobacter*, etc.

Examples of fungal cells include, but are not limited to, cells from organisms such as dermatophytes (e.g., *Microsporum canis* and other *Microsporum* sp.; and *Trichophyton* sp. such as *T. rubrum*, and *T. mentagrophytes*), *Torulopsis glabrata, Epidermophyton floccosum, Malassezia furfur* (*Pityropsporon orbiculare*, or *P. ovale*), *Cryptococcus neoformans, Aspergillus* species (including *A. fumigatus, A. nidulans*, and other *Aspergillus* species), Zygomycetes (e.g., *Rhizopus, Mucor*), *Paracoccidioides brasiliensis, Blastomyces dermatitides, Histoplasma capsulatum, Coccidioides immitis*, and *Sporothrix schenckii*, etc. The bioactive particulate can be a yeast cell. Examples of yeast cells include *Candida albicans, C. Tropicalis*, or other *Candida* species, *Saccharomyces* species such *S. cerevisiae, S. pastorianus, S. bayanum*, etc.

The cells can be derived from a natural source, genetically engineered, or produced by any other means. Any natural source of eukaryotic or prokaryotic cells can be used. In an embodiment, the natural source is a mammal. In an embodiment, the mammal is human.

The cells can be engineered to express one or more genes, repress the expression of one or more genes, or both. An example of genetically engineered cells useful in the system and methods of the present invention are cells engineered to make and secrete one or more desired bioactive molecules, including antibodies and recombinant proteins having therapeutic activity. In an embodiment, the cells are hydridoma cells producing a monoclonal antibody. The term "antibody" is used in the broadest sense and specifically includes single monoclonal antibodies (including agonist and antagonist antibodies), antibody compositions with polyepitopic specificity, affinity-matured antibodies, humanized antibodies, chimeric antibodies, single chain antigen binding molecules such as monobodies, as well as antigen binding fragments or polypeptides (e.g., Fab, F(ab')$_2$, scFv, and Fv) that exhibit a desired biological activity.

Examples of bioactive molecules include growth factors, differentiation factors, antibodies, and hormones. The antibodies can be monoclonal. The antibodies can be chimeric or humanized. Examples of hormones include insulin, human growth factor, erythropoietin, thyroid stimulating hormone, estrogen, or progesterone. Cells can be engineered to produce an antigen for use in a vaccine. Cells can be engineered to produce bioactive molecules that inhibit or stimulate inflammation, facilitate healing, resist immuno-rejection, provide hormone replacement, replace neurotransmitters, inhibit or destroy cancer cells, promote cell growth, inhibit or stimulate formation of blood vessels, augment tissue, and promote or induce supplementation or replacement of skin, synovial fluid, tendons, cartilage, ligaments, bone, muscle, organs, dura, blood vessels, bone marrow, and extracellular matrix.

Genetic engineering can involve, for example, adding or removing genetic material to or from a cell, altering existing genetic material, or both using standard recombinant methods. Embodiments in which cells are transfected or otherwise engineered to express a gene can use transiently or permanently transfected genes, or both. Gene sequences can be full or partial length, cloned or naturally occurring.

The term "bioactive molecule" as used herein means a molecule that has an effect on a cell or tissue. The term includes vitamins, salts, electrolytes, amino acids, peptides, polypeptides, proteins, carbohydrates, lipids, polysaccharides, nucleic acids, nucleotides, polynucleotides, glycoproteins, lipoproteins, glycolipids, glycosaminoglycans, proteoglycans, growth factors, differentiation factors, hormones, neurotransmitters, pheromones, chalones, prostaglandins, immunoglobulins, monokines and other cytokines, humectants, minerals, electrically and magnetically reactive materials, light sensitive materials, heat-sensitive materials, antioxidants, molecules that can be metabolized as a source of cellular energy, antigens, and any molecules that can cause a cellular or physiological response. Any combination of molecules can be used, as well as agonists or antagonists of these molecules. Glycosaminoglycans include glycoproteins, proteoglycans, and hyaluronan. Polysaccharides include cellulose, starch, alginic acid, chitosan, or hyaluronan. Cytokines include, but are not limited to, cardiotrophin, stromal cell derived factor, macrophage derived chemokine (MDC), melanoma growth stimulatory activity (MGSA), macrophage inflammatory proteins 1 alpha (MIP-1 alpha), 2, 3 alpha, 3 beta, 4 and 5, interleukin (IL) 1, IL-2, IL-3, IL-4, IL-5, IL-6, IL-7, IL-8, IL-9, IL-10, IL-11, IL-12, IL-13, TNF-alpha, and TNF-beta. Immunoglobulins useful in the present invention include, but are not limited to, IgG, IgA, IgM, IgD, IgE, and mixtures thereof. Amino acids, peptides, polypeptides, and proteins can include any type of such molecules of any size and complexity as well as combinations of such molecules. Examples include, but are not limited to, structural proteins, enzymes, and peptide hormones.

The term bioactive molecule also includes fibrous proteins, adhesion proteins, adhesive compounds, targeting compounds, growth inhibitors, and differentiation inhibitors. Fibrous proteins include collagen and elastin. Adhesion/deadhesion compounds include fibronectin, laminin, thrombospondin and tenascin C. Adhesive proteins include actin, fibrin, fibrinogen, fibronectin, vitronectin, laminin, cadherins, selecting, intracellular adhesion molecules 1, 2, and 3, and cell-matrix adhesion receptors including but not limited to integrins such as $\alpha_5\beta_1$, $\alpha_6\beta_1$, $\alpha_7\beta_1$, $\alpha_1\beta_2$, $\alpha_2\beta_3$, and $\alpha_6\beta_4$. Growth inhibitors include bone marrow stromal cell derived growth inhibitor, p21(WAF1/Cip1) cell cycle inhibitor, and taxol. Differentiation inhibitors include thrombospondin and Nogo-A.

The term bioactive molecule also includes leptin, leukemia inhibitory factor (LIF), RGD peptide, tumor necrosis factor alpha and beta, endostatin, angiostatin, thrombospondin, osteogenic protein-1, bone morphogenic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18.

The term "growth factor" as used herein means a bioactive molecule that promotes the proliferation of a cell or tissue. Growth factors useful in the present invention include, but are not limited to, transforming growth factor-alpha (TGF-alpha), transforming growth factor-beta (TGF-beta), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some growth factors can also promote differentiation of a cell or tissue. TGF, for example, can promote growth and/or differentiation of a cell or tissue. Some preferred growth factors include VEGF, NGFs, PDGF-AA, PDGF-BB, PDGF-AB, FGFb, FGFa, and BGF.

The term "differentiation factor" as used herein means a bioactive molecule that promotes the differentiation of cells. The term includes, but is not limited to, neurotrophin, colony stimulating factor (CSF), or transforming growth factor. CSF includes granulocyte-CSF, macrophage-CSF, granulocyte-macrophage-CSF, erythropoietin, and IL-3. Some differentiation factors can also promote the growth of a cell or tissue. TGF and IL-3, for example, can promote differentiation and/or growth of cells.

In an embodiment, growth factor(s) and/or differentiation factor(s) is released by the fine fiber layer. The rate of release of the growth factors or differentiation factors is determined by the rate of degradation or dissolution of the fiber layer.

The term "adhesive compound" as used herein means a bioactive molecule that promotes attachment of a cell through the formation of focal adhesion complexes to a fiber surface comprising the adhesive compound. Examples of adhesive compounds include, but are not limited to, fibronectin, vitronectin, laminin, or fragments thereof.

The term "targeting compound" as used herein means a bioactive molecule that functions as a signaling molecule inducing recruitment and/or attachment of cells to a fiber comprising the targeting compound. Examples of targeting compounds and their cognate receptors include attachment peptides including RGD peptide derived from fibronectin and integrins, growth factors including EGF and EGF receptor, and hormones including insulin and insulin receptor.

A fibrous structure or substrate of the invention can also include an active and/or inert particulate dispersed in the fiber layer(s). The particulate materials of the invention have dimensions capable of improving the active properties and filtration or purification properties of the media and layers of the invention. The materials can be made of a variety of useful materials that are inert, reactive, absorptive, or adsorptive. In bioprocessing and bioconversion applications utilizing cells or microorganisms, the active or inert particulates are preferably non-cytotoxic. The materials can either be substantially inert to the mobile phase and entrained particulate or dissolved chemical contaminate load passing through the web or the materials can interact with the fluid, dissolved portions of the fluid or the particulate loading in the fluid. Some or all of the particulate can be inert. Preferred particulates are active, bioactive, reactive, absorbent, or adsorbent materials. For the purpose of this invention, the term "inert" indicates that the material in the web does not either substantially chemically react with the fluid or particulate loading, or substantially physically absorb or adsorb a portion of the fluid or the particulate loading onto the particulate in any substantial quantity. In this "inert" mode, the particulate simply alters the physical parameters of the fiber layer and the media including one or more fiber layers. Such particles can be used as a separation means or to occupy space. Inert particles can be coated with an enzyme or other bioactive molecule using conventional methods. In an embodiment, the inert particle is a polymeric bead.

The term "active particulate", when used in this disclosure, refers to the absorptive, adsorptive or reactive particulate. For the purpose of this patent application, the term "adsorptive" indicates a particle that is active to adsorb and accumulate material from a fluid stream on the surface of a particle. The term "absorptive" indicates that the particle has the capacity to accumulate material from a fluid stream into the interior or void space or spaces within a particle. "Chemically reactive" indicates that the particulate has the capacity to react with and chemically change both the character of the particle and the chemical character of the material in the fluid stream.

The active particulate of the invention can be added to any layer of the element of the invention using a variety of add on techniques. The particulate of the invention can comprise an inert particulate coated with or otherwise attached to a cell, microorganism, enzyme or bioactive molecule, or combined with an active or bioactive particulate. The particulate of the invention can be incorporated into the fine fiber layer during spinning of the fiber as discussed elsewhere in the application. In addition, the active particulate of the invention can be dissolved or dispersed into an aqueous or nonaqueous or mixed aqueous liquid and applied to any layer of a useful element of the invention.

When using an active particulate that interacts with the fluid or the particulate loading, the particulate can, in addition to altering the physical properties of the media or layers, react with or absorb or adsorb a portion of either the mobile fluid or the particulate loading for the purpose of altering the material that passes through the web. The primary focus of the technology disclosed herein is to improve the treatment properties of the layers to increase the bioactivity/reactivity/absorbent/adsorbent capacity or lifetime of the physical structure of the media or layers, and to improve filter performance in purification methods as needed. In many such applications, a combination of an inert particle, active particle, and bioactive particle will then be used.

The particulate can take a variety of regular geometric shapes or amorphous structures. Such shapes can include amorphous or random shapes, agglomerates, spheres, discs, ovals, extended ovals, cruciform shapes, rods, hollow rods or cylinders, bars, three dimensional cruciform shapes having multiple particulate forms extending into space, hollow spheres, non-regular shapes, cubes, solid prisms of a variety of faces, corners and internal volumes. The aspect ratio of the non-spherical particulate (the ratio of the least dimension of the particle to the major or largest dimension) of the invention can range from about 1:2 to about 1:10, preferably from about 1:2 to about 1:8.

The particulate of the invention is either a non-interacting inert particulate, or a bioactive particulate that forms part of the multilamellar nanofibrillar matrix of the invention. The particulate that is non-interacting with the mobile fluid or entrained particulate phase comprises both organic and inorganic materials. Organic particulates can be made from polystyrene or styrene copolymers expanded or otherwise, nylon or nylon copolymers, polyolefin polymers including polyethylene, polypropylene, ethylene, olefin copolymers, propylene olefin copolymers, acrylic polymers and copolymers including polymethylmethacrylate, and polyacrylonitrile. Further, the particulate can comprise cellulosic materials and cellulose derivative beads. Such beads can be manufactured from cellulose or from cellulose derivatives such as methyl cellulose, ethyl cellulose, hydroxymethyl cellulose, hydroxyethyl cellulose, and others. Further, the particulates can comprise a diatomaceous earth, zeolite, talc, clay, silicate, fused silicon dioxide, glass beads, ceramic beads, metal particulates, metal oxides, etc. Particulates intended for use in the present invention are characterized by average size in the range of from about 0.01 to 510 microns. Although submicron active particles are used, the present invention is applicable to fine particles up to 100 microns in average size. In any event, the average size of the active particles will be on the order of approximately 0.01 to 0.0001 of the average size of the particulates. Therefore, a relatively larger average size of the active particles requires a larger average size of the particulate. Particles include carbon particles such as activated carbon, ion exchange resins/beads, zeolite particles, diatomaceous earth, alumina particles such as activated alumina, polymeric particles including, for example, styrene monomer, and absorbent particles such as commercially available superabsorbent particles.

Particularly suitable absorbent/adsorbent particles are low density, porous particles, and have pores and cavities including surface cavities, ranging in diameter from about 1 to 100 microns and interconnected by smaller pores. These pores and cavities beneficially provide inner surface for deposition, in particular monolayer deposition, of fine particles having an average size in the range of about 0.01 to 10 microns, and thereafter for accessibility to the immobilized fine particles. 1 $cm^3$ of these particles provides in bulk approximately 75 to 1,500 $m^2$ of available surface. Carbon particulates can be used in the form of filing divided activated carbon. Such activated carbons can be combined with other reactive adsorbent or adsorbent species that can be blended with, or adsorbed onto, the carbon surface. Other forms of active carbon can be used including carbon nanotubes, nanoparticles, nanowires, nanocarbon ropes or larger lattices or constructs in which the individual elements comprise a carbon nanotube. Such nanoparticles, such as buckyballs, smaller nanotubes (or nanotube portions thereof), nanoropes, etc. can be incorporated within the interior volume of the nanotube or incorporated into the carbon atom lattice of the nano structure. Additional atoms, molecules or components can add structure or function to the nano particulate material.

The particulate of the invention can be photoreactive, magnetic or conductive. Photoreactive particle include metal oxide particles such as catalytic $TiO_2$ particles. The fibers, or layers, in the element of the invention may also be photoreactive, magnetic, or conductive. Such catalytic layers, when irradiated with UV light, can cause a chemical reaction between the catalyst and materials entrapped in the mobile phase, and can remove the materials or change them from a noxious or harmful material into a benign material. Ambient light can often be the source of sufficient radiation energy to obtain the catalytic effect for the $TiO_2$ in the element. If ambient conditions are insufficient for activity the element can be used with a separate UV source. Fluorescent UV sources are known and can be used either as a separate irradiating source, or can be incorporated into the element to provide substantial amount of UV radiation onto the $TiO_2$. Magnetic materials for use as the particulate or nanofiber layer of the invention include ferritin, The particulate of the invention can be magnetic, such as ferritin, for example.

Small molecule, oligomeric and polymeric materials can be used in the invention. Small molecules typically have molecular weights of less than about 500, are typically made up of a single identifiable molecular unit and typically the units do not repeat in the molecular structure. Oligomer structures typically have somewhat larger molecular weights but typically have 2 to 10 repeating molecular units in a structure. Polymer units typically have substantially higher molecular weights and typically have substantially greater than 10 repeating units in a polymer structure. The differentiation between oligomeric and polymeric structures is not always clear cut; however, as the number of repeat units in the structure increases, the material tends to become more polymeric in nature.

The particulate can be mono-disperse or poly-disperse. In mono-disperse particulate, the majority of the particles are similar in diameter or the major dimension. For example, one example of a mono-disperse particulate has 80% to 90% of the particulate within about 0.8±0.5 microns or about 1±0.25 micron. In a poly-disperse material, the particulate has a substantial portion of particles with different diameters. A poly-disperse material could be a mixture of two mono-disperse materials or a material with a substantial amount of particulate material present throughout a broad range (e.g.) 0.1 to 10 or 0.01 to 100 microns.

The spheres or other shapes can be in a variety of different physical forms including solid and hollow form. The particulate can have a substantially spherical or slightly oval shaped spherical structure. The spheres can be solid or can have a substantial internal void volume. The shell thickness of the sphere can range from about 0.05 to about 500 microns while the sphere can range from about 0.5 to about 5000 microns. Other circular structures that can be used include simple toroidal structures, spiral or helical structures, or interlocking link type chain structures.

The particulate of the invention can also comprise a bioactive or reactive absorbent or adsorbent fiber-like structure having a predetermined length and diameter. The aspect ratio of such a fiber is typically about 1 to about 10:1 having a fiber diameter that is typically larger in diameter than the fine fiber of the structure. The diameter ratio of the particulate fiber to the fine fiber is typically about 0.5 to about 5000:1. A variety of other regular shapes can be used including cylindrical, hollow cylindrical, cruciform structures, three-dimensional cruciform structures, I-beam structures, and others. The particulate can also be irregular in shape such that the particulate has a relatively well-defined major and minor dimension but has an exterior surface that is substantially irregular in nature. Many amorphous organic and inorganic particulates can have an irregular shape, but can have a size that can provide the spacing property of the particulate material. Depending upon the physical form and chemical nature of the spheres, the dimensions of the spheres can be manipulated by a secondary process such as super absorbency, solvent swelling, heat expansion, porosity changes, etc. Microspheres available from Expancel® can be heat-treated to expand the volume of the microspheres tremendously. Fine fiber and microsphere composite media can be produced according to this invention, and later upon a secondary treatment—not limited to heat—the structure of the composite media can be tuned in a controlled way, for example in the Expancel® case, depending upon the level of applied heat and temperature, one can control the degree of expansion of the microspheres. For example, by expanding the microspheres, the thickness and loftiness of the structure can be increased and thereby filtration properties can be altered in a desired way. It should be understood that such changes in the physical nature of the microsphere should be accommodated by the elasticity of the fine fiber as they would stretch in the case of expansion of the microspheres. Depending upon the reversibility of the change in microspheres, one can also create lofty structures and then collapse/shrink the structure to create dense/compact filtration structures.

Particulate material and fine fiber layers of the invention can also be used as substrates for the culture of organisms and enzymes. Such materials are non-toxic and biocompatible materials designed to serve as scaffolds and three-dimensional spatial organizers. The substrate may be any surface that offers structural support for the deposited network of nanofibers. The substrate may comprise glass or plastic. Preferably the plastic is non-cytotoxic. The substrate may be a film or culture container. The substrate may be water soluble or water insoluble. A substrate that is water soluble is preferably a polyvinyl alcohol film. The substrate may be porous or non-porous. Porosity of the substrate is determined by cellular penetration. A cell is able to penetrate a porous substrate but is not able to penetrate a non-porous substrate. The substrate may be biodegradable and/or biodesolvable. Preferably the substrate is biocompatible.

The substrate may comprise one or more bioactive molecules, or particulates. Preferably one of the bioactive molecules is a peptide, polypeptide, lipid, carbohydrate, polysaccharide, amino acid, or hybrid molecule thereof. The substrate may comprise one or more alcohol, aldehyde, amino, carboxy, sulphydryl or photoactivatable functional groups. Preferably the photoactivatable group is a carbene or nitrene. The substrate may comprise one or more growth factors and/or differentiation factors. The substrate may release one or more growth factors and/or differentiation factors. The rate of release is determined by the rate of dissolution or degradation of the substrate.

The substrate may comprise one of more bioactive molecules, of particulates that make up a culture container. The term "culture container" as used herein means a receptacle for holding media for culturing a cell or tissue. The culture container may be glass or plastic. Preferably the plastic is non-cytotoxic. The term culture container includes, but is not limited to, single and multiwell culture plates, chambered and multi-chambered culture slides, cups, flasks, tubes, bottles, roller bottles, spinner bottles, perfusion chambers, and fermenters.

The web of the invention can be used in bioreactor applications and filtration or fluid purification applications as a surface media or depth media having a continuous web of fine fiber modified by the presence of a reactive, absorptive, adsorptive, or bioactive spacer or separation means in the form of a particulate that in combination with the fiber in the media, provides filtration efficiency, filtration permeability, depth loading, extended useful lifetime characterized by minimal pressure drop increase, or a combination thereof. The bioactive, reactive, absorptive, or adsorptive spacer or separation means causes the fiber web to attain a structure, in which the fiber mass or web portion has reduced solidity, separated fibers or separated web portions within the structure, and increased depth of fiber layer, without increasing the amount of polymer or the number of fibers in the web. The reactive, adsorptive, absorptive, or bioactive portion of the fiber web can react with reactive chemical species within a mobile fluid passing through the fiber layer or such chemical components of the mobile fluid can be absorbed or adsorbed by the absorptive or adsorptive portion of the fiber layer. The active or bioactive particulate can be used with an inert particulate as long as the activity or activities of the particulate is maintained. In filtration applications, the resulting structure obtains improved filtration properties in combination with resistance to increased pressure drop, improved permeability, improved efficiency, and the ability to remove both a particulate non-reactive load and a reactive gaseous or particulate load from a mobile fluid stream passing through the fiber layer. With respect to filter applications of the invention, a "fluid stream" indicates a liquid stream that can contain a particulate. The particulate can be either filtered from the fluid stream or the particulate can be adsorbed, absorbed or reacted with the particulate material of the invention.

The fine fiber/nanofiber layer of the invention can be made from a variety of polymeric species. Polymer materials that can be used as the fiber polymer compositions of the invention include both addition polymer and condensation polymer materials such as polyolefin, polyacetal, polyamide, polyester, cellulose ether and ester, polyalkylene sulfide, polyarylene oxide, polysulfone, modified polysulfone polymers and mixtures thereof. Preferred materials that fall within these generic classes include polyethylene, polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinylalcohol in various degrees of hydrolysis (80% to 99.5%) in crosslinked and non-crosslinked forms. Preferred addition polymers tend to be glassy (a glass transition temperature ($T_g$) greater than room temperature). This is the case for polyvinylchloride and polymethylmethacrylate, polystyrene polymer compositions or alloys or low in crystallinity for polyvinylidene fluoride and polyvinylalcohol materials. One class of polyamide condensation polymers are nylon materials. The term "nylon" is a generic name for all long chain synthetic polyamides. Typically, nylon nomenclature includes a series of numbers such as in nylon-6,6 which indicates that the starting materials are a $C_6$ diamine and a $C_6$ diacid (the first digit indicating a $C_6$ diamine and the second digit indicating a $C_6$ dicarboxylic acid compound). Nylon can be made by the polycondensation of ε-caprolactam in the presence of a small amount of water. This reaction forms a nylon-6 (made from a cyclic lactam—also known as ε-aminocaproic acid) that is a linear polyamide. Further, nylon copolymers are also contemplated. Copolymers can be made by combining various diamine compounds, various diacid compounds and various cyclic lactam structures in a reaction mixture and then forming the nylon with randomly positioned monomeric materials in a polyamide structure. For example, a nylon 6,6-6,10 material is a nylon manufactured from hexamethylene diamine and a $C_6$ and a $C_{10}$ blend of diacids. A nylon 6,6-6,6,10 is a nylon manufactured by copolymerization of E-aminocaproic acid, hexamethylene diamine and a blend of a $C_6$ and a $C_{10}$ diacid material.

Block copolymers are also useful in the process of this invention. With such copolymers the choice of solvent swelling agent is important. The selected solvent is such that both blocks were soluble in the solvent. One example is a ABA (styrene-EP-styrene) or AB (styrene-EP) polymer in methylene chloride solvent. If one component is not soluble in the solvent, it will form a gel. Examples of such block copolymers are Kraton® type of styrene-b-butadiene and styrene-b-hydrogenated butadiene (ethylene propylene), Pebax® type of ε-caprolactam-b-ethylene oxide, Sympatex® polyester-b-ethylene oxide and polyurethanes of ethylene oxide and isocyanates. Biocompatible polymers useful in the process of this invention include, for example, polyester, poly(ε-caprolactone), polyglycolate, polylactate, polyamide, nylon, and mixtures or combinations thereof.

Addition polymers like polyvinylidene fluoride, syndiotactic polystyrene, copolymer of vinylidene fluoride and hexafluoropropylene, polyvinyl alcohol, polyvinyl acetate, amorphous addition polymers, such as poly(acrylonitrile) and its copolymers with acrylic acid and methacrylates, polystyrene, poly(vinyl chloride) and its various copolymers, poly(methyl methacrylate) and its various copolymers, can be solution spun with relative ease because they are soluble at low pressures and temperatures. However, highly crystalline polymer like polyethylene and polypropylene require high temperature, high pressure solvent if they are to be solution spun. Therefore, solution spinning of the polyethylene and polypropylene is very difficult. Electrostatic solution spinning is one method of making nanofibers and microfiber.

The polyurethane (PU) polyether used in this layer of invention can be an aliphatic or aromatic polyurethane depending on the isocyanate used and can be a polyether polyurethane or a polyester polyurethane. A polyether urethane having good physical properties can be prepared by melt polymerization of a hydroxyl-terminated polyether or polyester intermediate and a chain extender with an aliphatic or aromatic (MDI) diisocyanate. The hydroxyl-terminated polyether has alkylene oxide repeat units containing from 2 to 10 carbon atoms and has a weight average molecular weight of at least 1000. The chain extender is a substantially non-branched glycol having 2 to 20 carbon atoms. The amount of the chain extender is from 0.5 to less than 2 mole per mole of hydroxyl terminated polyether. It is preferred that the polyether polyurethane is thermoplastic and has a melting point of about 140° C. to 250° C. or greater (e.g., 150° C. to 250° C.) with 180° C. or greater being preferred.

In a first mode, the polyurethane polymer of the invention can be made simply by combining a di-, tri- or higher functionality aromatic or aliphatic isocyanate compound with a polyol compound that can comprise either a polyester polyol or a polyether polyol. The reaction between the active hydrogen atoms in the polyol with the isocyanate groups forms the addition polyurethane polymer material in a straight forward fashion. The OH:NCO ratio is typically about 1:1 leaving little or no unreacted isocyanate in the finished polymer. In any unreacted isocyanate compound, reactivity can be scavenged using isocyanate reactive compounds. In a second mode, the polyurethane polymer can be synthesized in a stepwise fashion from isocyanate terminated prepolymer materials. The polyurethane can be made from an isocyanate-terminated polyether or polyester. An isocyanate-capped polyol prepolymer can be chain-extended with an aromatic or aliphatic dihydroxy compound. The term "isocyanate-terminated polyether or polyurethane" refers generally to a prepolymer which comprises a polyol that has been reacted with a diisocyanate compound (i.e., a compound containing at least two isocyanate (—NCO) groups). In preferred form, the prepolymer has a functionality of 2.0 or greater, an average molecular weight of about 250 to 10,000 or 600-5000, and is prepared so as to contain substantially no unreacted monomeric isocyanate compound. The term "unreacted isocyanate compound" refers to free monomeric aliphatic or aromatic isocyanate-containing compound, i.e., diisocyanate compound which is employed as a starting material in connection with the preparation of the prepolymer and which remains unreacted in the prepolymer composition.

The term "polyol" as used herein, generally refers to a polymeric compound having more than one hydroxy (—OH) group, preferably an aliphatic polymeric (polyether or polyester) compound which is terminated at each end with a hydroxy group. The chain-lengthening agents are difunctional and/or trifunctional compounds having molecular weights of from 62 to 500 preferably aliphatic diols having from 2 to 14 carbon atoms, such as, for example, ethanediol, 1,6-hexanediol, diethylene glycol, dipropylene glycol and, especially, 1,4-butanediol. Also suitable, however, are diesters of terephthalic acid with glycols having from 2 to 4 carbon atoms, such as, for example, terephthalic acid bis-ethylene glycol or 1,4-butanediol, hydroxy alkylene ethers of hydroquinone, such as, for example, 1,4-di(B-hydroxyethyl)-hydroquinone, (cyclo)aliphatic diamines, such as, for example, isophorone-diamine, ethylenediamine, 1,2-, 1,3-propylene-diamine, N-methyl-1,3-propylene-diamine, N,N'-dimethyl-ethylene-diamine, and aromatic diamines, such as, for example, 2,4- and 2,6-toluylene-diamine, 3,5-diethyl-2,4- and/or -2,6-toluylene-diamine, and primary ortho- di-, tri- and/or tetra-alkyl-substituted 4,4'-diaminodiphenyl-methanes. It is also possible to use mixtures of the above-mentioned chain-lengthening agents. Preferred polyols are polyesters, polyethers, polycarbonates or a mixture thereof. A wide variety of polyol compounds is available for use in the preparation of the prepolymer. In preferred embodiments, the polyol may comprise a polymeric diol including, for example, polyether diols and polyester diols and mixtures or copolymers thereof. Preferred polymeric diols are polyether diols, with polyalkylene ether diols being more preferred. Exemplary polyalkylene polyether diols include, for example, polyethylene ether glycol, polypropylene ether glycol, polytetramethylene ether glycol (PTMEG) and polyhexamethylene ether glycol and mixtures or copolymers thereof. Preferred among these polyalkylene ether diols is PTMEG. Preferred among the polyester diols are, for example, polybutylene adipate glycol and polyethylene adipate glycol and mixtures or copolymers thereof. Other polyether polyols may be prepared by reacting one or more alkylene oxides having from 2 to 4 carbon atoms in the alkylene radical with a starter molecule containing two active hydrogen atoms bonded therein. The following may be mentioned as examples of alkylene oxides: ethylene oxide, 1,2-propylene oxide, epichlorohydrin and 1,2- and 2,3-butylene oxide. Preference is given to the use of ethylene oxide, propylene oxide and mixtures of 1,2-propylene oxide and ethylene oxide. The alkylene oxides may be used individually, alternately in succession, or in the form of mixtures. Starter molecules include, for example: water, amino alcohols, such as N-alkyldiethanolamines, for example N-methyl-diethanolamine, and diols, such as ethylene glycol, 1,3-propylene glycol, 1,4-butanediol and 1,6-hexanediol. It is also possible to use mixtures of starter molecules. Suitable polyether polyols are also the hydroxyl-group-containing polymerization products of tetrahydrofuran. Suitable polyester polyols may be prepared, for example, from dicarboxylic acids having from 2 to 12 carbon atoms, preferably from 4 to 6 carbon atoms, and polyhydric alcohols. Suitable dicarboxylic acids include, for example: aliphatic dicarboxylic acids, such as succinic acid, glutaric acid, adipic acid, suberic acid, azelaic acid and sebacic acid, and aromatic dicarboxylic acids, such as phthalic acid, isophthalic acid and terephthalic acid. The dicarboxylic acids may be used individually or in the form of mixtures, for example in the form of a succinic, glutaric and adipic acid mixture. It may be advantageous for the preparation of the polyester polyols to use, instead of the dicarboxylic acids, the corresponding dicarboxylic acid derivatives, such as carboxylic acid diesters having from 1 to 4 carbon atoms in the alcohol radical, carboxylic acid anhydrides or carboxylic acid chlorides. Examples of polyhydric alcohols are glycols having from 2 to 10, preferably from 2 to 6, carbon atoms, such as ethylene glycol, diethylene glycol, 1,4-butanediol, 1,5-pentanediol, 1,6-hexanediol, 1,10-decanediol, 2,2-dimethyl-1,3-propanediol, 1,3-propanediol and dipropylene glycol. According to the desired properties, the polyhydric alcohols may be used alone or, optionally, in admixture with one another. Also suitable are esters of carbonic acid with the mentioned diols, especially those having from 4 to 6 carbon atoms, such as 1,4-butanediol and/or 1,6-hexanediol, condensation products of (omega-hydroxycarboxylic acids, for example (omega-hydroxycaproic acid, and preferably polymerization products of lactones, for example optionally substituted (E-caprolactones. These are preferably used as polyester polyols ethanediol polyadipate, 1,4-butanediol polyadipate, ethanediol-1,4-butanediol polyadipate, 1,6-hexanediol neopentyl glycol polyadipate, 1,6-hexanediol-1,4-butanediol polyadipate and polycaprolactones. The polyester polyols have molecular weights of from 600 to 5000.

The number of average molecular weight of the polyols from which the polymer or prepolymers may be derived may range from about 800 to about 3500 and all combinations and subcombinations of ranges therein. More preferably, the number of average molecular weights of the polyol may range from about 1500 to about 2500, with number average molecular weights of about 2000 being even more preferred.

The polyol in the prepolymers can be capped with an isocyanate compound or can be fully reacted to the thermoplastic polyurethane (TPU). A wide variety of diisocyanate compounds is available for use in the preparation of the prepolymers of the present invention. Generally speaking, the diisocyanate compound may be aromatic or aliphatic, with aromatic diisocyanate compounds being preferred. Included among the suitable organic diisocyanates are, for example, aliphatic, cycloaliphatic, aralphatic, heterocyclic and aromatic diisocyanates, as are described, for example, in *Justus Liebigs Annalen der Chemie*, 562, pages 75 to 136. Examples of suitable aromatic diisocyanate compounds include diphenylmethane diisocyanate, xylene diisocyanate, toluene diisocyanate, phenylene diisocyanate, and naphthalene diisocyanate and mixtures thereof. Examples of suitable aliphatic diisocyanate compounds include dicyclohexylmethane diisocyanate and hexamethylene diisocyanate and mixtures thereof. Preferred among the diisocyanate compounds is MDI due, at least in part, to its general commercial availability and high degree of safety, as well as its generally desirable reactivity with chain extenders (discussed more fully hereinafter). Other diisocyanate compounds, in addition to those exemplified above, would be readily apparent to one of ordinary skill in the art, once armed with the present disclosure. The following may be mentioned as specific examples: aliphatic diisocyanates, such as hexamethylene diisocyanate, cycloaliphatic diisocyanates, such as isophorone diisocyanate, 1,4-cyclohexane diisocyanate, 1-methyl-2,4- and -2,6-cyclohexane diisocyanate and the corresponding isomeric mixtures, 4,4'-, 2,4'- and 2,2'-dicyclohexylmethane diisocyanate and the corresponding isomeric mixtures, and, preferably, aromatic diisocyanates, such as 2,4-toluylene diisocyanate, mixtures of 2,4- and 2,6-toluylene diisocyanate, 4,4'-, 2,4'- and 2,2'-diphenylmethane diisocyanate, mixtures of 2,4'- and 4,4'-diphenylmethane diisocyanate, urethane-modified liquid 4,4'- and/or 2,4'-diphenylmethane diisocyanates, 4,4'-diisocyanatodiphenylethane-(1,2) and 1,5-naphthylene diisocyanate. Preference is given to the use of 1,6-hexamethylene diisocyanate, isophorone diisocyanate, dicyclohexylmethane diisocyanate, diphenylmethane diisocyanate isomeric mixtures having a 4,4'-diphenylmethane diisocyanate content of greater than 96 wt. %, and especially 4,4'-diphenylmethane diisocyanate and 1,5-naphthylene diisocyanate.

For the preparation of the TPUs, the chain-extension components are reacted, optionally in the presence of catalysts, auxiliary substances and/or additives, in such amounts that the equivalence ratio of NCO groups to the sum of all the NCO-reactive groups, especially of the OH groups of the low molecular weight diols/triols and polyols, is from 0.9:1.0 to 1.2:1.0, preferably from 0.95:1.0 to 1.10:1.0. Suitable catalysts, which in particular accelerate the reaction between the NCO groups of the diisocyanates and the hydroxyl groups of the diol components, are the conventional tertiary amines known in the prior art, such as, for example, triethylamine, dimethylcyclohexylamine, N-methylmorpholine, N,N'-dimethyl-piperazine, 2-(dimethylaminoethoxy)-ethanol, diazabicyclo-(2,2,2)-octane and the like, as well as, especially, organometallic compounds such as titanic acid esters, iron compounds, tin compounds, for example tin diacetate, tin dioctate, tin dilaurate or the tin dialkyl salts of aliphatic carboxylic acids, such as dibutyltin diacetate, dibutyltin dilaurate or the like. The catalysts are usually used in amounts of from 0.0005 to 0.1 part per 100 parts of polyhydroxy compound. In addition to catalysts, auxiliary substances and/or additives may also be incorporated into the chain-extension components. Examples which may be mentioned are lubricants, antiblocking agents, inhibitors, stabilizers against hydrolysis, light, heat and discoloration, flameproofing agents, colorings, pigments, inorganic and/or organic fillers and reinforcing agents. Reinforcing agents are especially fibrous reinforcing materials such as, for example, inorganic fibers, which are prepared according to the prior art and may also be provided with a size.

Further additional components that may be incorporated into the PU are thermoplastics, for example polycarbonates and acrylonitrile-butadiene-styrene terpolymers, especially ABS. Other elastomers, such as, for example, rubber, ethylene-vinyl acetate polymers, styrene-butadiene copolymers and other PUs, may likewise be used. Also suitable for incorporation are commercially available plasticisers such as, for example, phosphates, phthalates, adipates, sebacates. The PUs according to the invention are produced continuously. Either the known band process or the extruder process may be used. The components may be metered simultaneously, i.e. one shot, or in succession, i.e. by a prepolymer process. In that case, the prepolymer may be introduced either batchwise or continuously in the first part of the extruder, or it may be prepared in a separate prepolymer apparatus arranged upstream. The extruder process is preferably used, optionally in conjunction with a prepolymer reactor.

Fiber can be made by conventional methods and can be made by melt spinning the polyurethane PU or a mixed polyether urethane and the additive. Melt spinning is a well known process in which a polymer is melted by extrusion, passed through a spinning nozzle into air, solidified by cooling, and collected by winding the fibers on a collection device. Typically the fibers are melt-spun at a polymer temperature of about 150° C. to about 300° C.

Polymeric materials have been fabricated in non-woven and woven fabrics, fibers and microfibers. The polymeric material provides the physical properties required for product stability. These materials should not change significantly in dimension, suffer reduced molecular weight, become less flexible or subject to stress cracking, or physically deteriorate in the presence of sunlight, humidity, high temperatures or other negative environmental effects. The invention relates to an improved polymeric material that can maintain physical properties in the face of incident electromagnetic radiation such as environmental light, heat, humidity and other physical challenges.

We have also found a substantial advantage to forming polymeric compositions comprising two or more polymeric materials in polymer admixture, alloy format, or in a crosslinked chemically bonded structure. We believe such polymer compositions improve physical properties by changing polymer attributes such as improving polymer chain flexibility or chain mobility, increasing overall molecular weight and providing reinforcement through the formation of networks of polymeric materials.

In one embodiment of this concept, two related or unrelated polymer materials can be blended for beneficial properties. For example, a high molecular weight polyvinylchloride can be blended with a low molecular weight polyvinylchloride. Similarly, a high molecular weight nylon material can be blended with a low molecular weight nylon material. Further, differing species of a general polymeric genus can be blended. For example, a high molecular weight styrene material can be blended with a low molecular weight, high impact polystyrene. A nylon-6 material can be blended with a nylon copolymer such as a nylon-6,6-6,6,10 copolymer. Further, a polyvinylalcohol having a low degree of hydrolysis such as an 80-87% hydrolyzed polyvinylalcohol can be blended with a fully or superhydrolyzed polyvinylalcohol having a degree of hydrolysis between 98 and 99.9% and higher. All of these materials in admixture can be crosslinked using appropriate crosslinking mechanisms. Nylons can be crosslinked using crosslinking agents that are reactive with the nitrogen atom in the amide linkage. Polyvinylalcohol materials can be crosslinked using hydroxyl reactive materials such as monoaldehydes, such as formaldehyde, ureas, melamine-formaldehyde resin and its analogues, boric acids and other inorganic compounds. dialdehydes, diacids, urethanes, epoxies and other known crosslinking agents. Crosslinking technology is a well known and understood phenomenon in which a crosslinking reagent reacts and forms covalent bonds between polymer chains to substantially improve molecular weight, chemical resistance, overall strength and resistance to mechanical degradation.

We have found that additive materials can significantly improve the properties of the polymer materials in the form of a fine fiber. The resistance to the effects of heat, humidity, impact, mechanical stress and other negative environmental effect can be substantially improved by the presence of additive materials. We have found that while processing the microfiber materials of the invention, the additive materials can improve the oleophobic character, the hydrophobic character, and can appear to aid in improving the chemical stability of the materials. We believe that the fine fibers of the invention in the form of a microfiber are improved by the presence of these oleophobic and hydrophobic additives as these additives form a protective layer coating, ablative surface or penetrate the surface to some depth to improve the nature of the polymeric material. We believe the important characteristics of these materials are the presence of a strongly hydrophobic group that can preferably also have oleophobic character. Strongly hydrophobic groups include fluorocarbon groups, hydrophobic hydrocarbon surfactants or blocks and substantially hydrocarbon oligomeric compositions. These materials are manufactured in compositions that have a portion of the molecule that tends to be compatible with the polymer material affording typically a physical bond or association with the polymer while the strongly hydrophobic or oleophobic group, as a result of the association of the additive with the polymer, forms a protective surface layer that resides on the surface or becomes alloyed with or mixed with the polymer surface layers. For 0.2-micron fiber with 10% additive level, the surface thickness is calculated to be around 50 Å, if the additive has migrated toward the surface. Migration is believed to occur due to the incompatible nature of the oleophobic or hydrophobic groups in the bulk material. A 50 Å thickness appears to be reasonable thickness for protective coating. For 0.05-micron diameter fiber, 50 Å thickness corresponds to 20% mass. For 2 microns thickness fiber, 50 Å thickness corresponds to 2% mass. Preferably the additive materials are used at an amount of about 2 to 25 wt. %. Oligomeric additives that can be used in combination with the polymer materials of the invention include oligomers having a molecular weight of about 500 to about 5000, preferably about 500 to about 3000 including fluoro-chemicals, nonionic surfactants and low molecular weight resins or oligomers. Examples of useful phenolic additive materials include Enzo-BPA, Enzo-BPA/phenol, Enzo-TBP, Enzo-COP and other related phenolics were obtained from Enzymol International Inc., Columbus, Ohio.

An extremely wide variety of fibrous filter media exist for different applications. The durable nanofibers and microfibers described in this invention can be added to any of the media. The fibers described in this invention can also be used to substitute for fiber components of these existing media giving the significant advantage of improved performance (improved efficiency and/or reduced pressure drop) due to their small diameter, while exhibiting greater durability.

Polymer nanofibers and microfibers are known; however, their use has been very limited due to their fragility to mechanical stresses, and their susceptibility to chemical degradation due to their very high surface area to volume ratio. The fibers described in this invention address these limitations and will therefore be usable in a very wide variety of bioprocessing, bioconversion, biosynthesis, filtration/purification, textile, membrane, and other diverse applications.

For applications in which the bioactive particulate is a cell or microorganism, the nanofibers of the invention, or the web or element of the invention, preferably comprise a non-cytotoxic polymer. Methods for determining the cytotoxicity of a polymer are known. Non-cytotoxic polymers can be identified using conventional methods. Examples of non-cytotoxic polymers include, but are not limited to, polyester, poly (ε-caprolactone), polyglycolate, polylactate, polyamides (including various nylon 6,6 and nylon 6,6-6,6,10). The polymer can be water soluble or water insoluble. The polymer can be biodegradable and/or biodissolvable. The polymer can comprise a first polymer and a second, but different polymer (differing in polymer type, molecular weight or physical property) conditioned or treated at elevated temperature. Since polymer species include a vast array of polymer materials, the polymer can be a single polymer species or blend of polymeric species or a polymer alloy of two or more polymer species.

The fibers can be made using any known fine fiber manufacturing technique that involves combining polymers, if necessary with other polymers or additives, and then using a forming technique to shape the polymer into the fine fiber polymer desired. An electrostatic spinning process can be used to form the fine fibers of the invention. A suitable apparatus for forming the fiber is illustrated in Barris U.S. Pat. No. 4,650,506. This apparatus includes a reservoir in which the fine fiber forming polymer solution is contained, a pump and a rotary type emitting device or emitter to which the polymeric solution is pumped. The emitter generally consists of a rotating union, a rotating portion including a plurality of offset holes and a shaft connecting the forward facing portion and the rotating union. The rotating union provides for introduction of the polymer solution to the forward facing portion through the hollow shaft. Alternatively, the rotating portion can be immersed into a reservoir of polymer fed by reservoir and pump. The rotating portion then obtains polymer solution from the reservoir and as it rotates in the electrostatic field, the electrostatic field aligned toward the collecting media accelerates a droplet of the solution as discussed below.

Facing the emitter, but spaced apart therefrom, is a substantially planar grid upon which the collecting media (i.e. substrate or combined substrate is positioned. Air can be drawn through the grid. The collecting media is passed around rollers which are positioned adjacent opposite ends of grid. A high voltage electrostatic potential is maintained between emitter and grid by means of a suitable electrostatic voltage source and connections and which connect respectively to the grid and emitter.

In use, the polymer solution is pumped to the rotating union or reservoir from reservoir. The forward facing portion rotates while liquid exits from holes, or is picked up from a reservoir, and moves from the outer edge of the emitter toward collecting media positioned on the grid. Specifically, the electrostatic potential between grid and the emitter imparts a charge to the material that cause liquid to be emitted there from as thin fibers which are drawn toward grid where they arrive and are collected on substrate or an efficiency layer. In the case of the polymer in solution, solvent is evaporated from the fibers during their flight to the grid; therefore, the fibers arrive at the substrate or efficiency layer without substantial solvent. The fine fibers bond to the substrate fibers first encountered at the grid. Electrostatic field strength is selected to ensure that as the polymer material it is accelerated from the emitter to the collecting media, the acceleration is sufficient to render the material into a very thin microfiber or nanofiber structure. Increasing or slowing the advance rate of the collecting media can deposit more or less emitted fibers on the forming media, thereby allowing control of the thickness of each layer deposited thereon. The rotating portion can have a variety of beneficial positions. The rotating portion can be placed in a plane of rotation such that the plane is perpendicular to the surface of the collecting media or positioned at any arbitrary angle. The rotating media can be positioned parallel to or slightly offset from parallel orientation.

A sheet-like substrate is unwound at a station. The sheet-like substrate is then directed to a splicing station wherein multiple lengths of the substrate can be spliced for continuous operation. The continuous length of sheet-like substrate is directed to a fine fiber technology station comprising the spinning technology discussed above, wherein a spinning device forms the fine fiber and lays the fine fiber in a filtering layer on the sheet-like substrate. After the fine fiber layer is formed on the sheet-like substrate in the formation zone, the fine fiber layer and substrate are directed to a heat treatment station for appropriate processing. The sheet-like substrate and fine fiber layer is then tested in an efficiency monitor and nipped if necessary at a nip station. The sheet-like substrate and fiber layer is then steered to the appropriate winding station to be wound onto the appropriate spindle for further processing.

Once the fine fiber layer containing the active or active inert particulate of the invention is prepared, the layer must be mechanically assembled into a useful active or adsorbent or absorbent structure. Nanofiber layers are typically spun onto a substrate material which can be a scrim, a cellulosic substrate, a mixed synthetic cellulosic substrate, such as a substrate comprising cellulosic fibers and non-cellulosic stabilizing fibers, or a purely cellulosic substrate. The nanofiber layers containing the active or inert particulate are electrospun onto said substrates and the substrate can then be rolled into an absorbent structure. Alternatively, the layer can be cut into similar portions and stacked to form an absorbent layer. It is important that the internal structure of any assembly of the nanofiber layers has sufficient fluid flow to ensure that the fluid can pass easily through the assembly. In this case, the assembly would act, not as a filter, but purely as an absorbent assembly structure. In an alternative structure, the layers of fine fiber and bioactive or active particulate can be assembled into a structure that filters or purifies, and reacts, adsorbs, or absorbs. Such varying structures have applications in a variety of end uses. The former structure has little or no filtration properties and can remove reactive contaminant materials from fluid streams such as wastewater streams (i.e. purify the wastewater streams), simply using a flow-through mechanism. The latter structure can remove particulate contaminate, either physically, or by chemical inactivation through oxidation or reduction of the contaminate. The structure can also remove chemical species (such as ions or dissolved organics, for example) from a fluid such as wastewater, simultaneously with the filtration or purification operations.

In certain preferred arrangements of the wound or stacked layers of the invention, the media can be configured for purification by a straight through flow either in a flow without filtration properties or a flow including passage through a filter layer. In such a fluid flow, the fluid will enter in one direction through a first flow face and exit moving in the same direction from a second flow face. Within the filter structure, the fluid may not interact with a surface that acts as a filter or it may interact with a flow, may contact a surface that obtains filtration properties. Generally, one preferred filter construction is a wound construction including a layer of media that is turned repeatedly about a center point forming a coil such that the filter media will be rolled, wound or coiled. One preferred useful structure is a corrugated structure in which the material has a fluted construction. Such flutes can be formed and combined with a face sheet. Once the corrugated media is combined with the uncorrugated media in the form of a face sheet, the resulting structure can be coiled and formed into a useful assembly. When using this type of media construction, the flutes form alternating peaks and troughs in the corrugated structure. In certain constructions, the upper flutes form flute chambers which can be closed at a downstream and while the flute chambers have upstream ends that are closed to form other rows of flutes. In such a structure, the opened and closed areas cause the fluid to pass through at least one corrugated wall to obtain filtration properties from the corrugated layer. In use, such corrugated media in a coiled assembly provides an intake area for a fluid stream such as wastewater. The fluid stream enters a flute chamber in an open upstream end, the unfiltered fluid flow is not permitted to pass through a closed down stream end but is forced to proceed through a corrugated layer or fluted sheet to contact either the fiber of the corrugated layer or the active particulate to either filter particulate from the fluid stream, or to ensure that the material dispersed or dissolved in the fluid stream is reacted with, absorbed, or adsorbed onto the active particulate, thereby purifying the fluid stream through the removal of chemical species present in the fluid stream.

The invention also relates to a membrane or membrane-like layer having a structure resulting from the polymeric material in the form of fine fiber. The membrane is formed by heat treating the fine fiber and the particulate to form a porous membrane. The membrane is a substantially continuous membrane or film-like layer having the particulate adhered to the surface of the membrane, imbedded into the membrane, or fully surrounded by the membrane polymer mass. In the membrane of the invention, the particulate can have a major dimension of less than 200 microns and typically has a dimension of about 0.05 to 100 microns or about 0.1 to 70 microns. The thickness of the membrane typically ranges from about 25 nm to 2 microns, or 0.5 to about 5 microns having a pore size that ranges from about 0.1 to 5 microns, often about 1 to 2 microns. The preferred membrane has a thickness of less than about 2 microns, and a pore size of about 0.1 to 2 microns, or 0.5 to 3 microns. The particulate is present in the membrane structure in an amount of about 0.1 to 50 vol %. Lastly, in the membrane, the particulate is available in the membrane layer in an amount of up to about 10 kg-m$^{-2}$ typically about 0.1 to 1,000 gm-m$^{-2}$, about 0.5 to 200 gm-m$^{-2}$ or about 1 to 100 gm-m$^{-2}$ of the membrane.

The fine fiber of the invention can be in the form of a structural fiber. The fine fiber can be spun from a reactive (i.e. chemically reactive, photoreactive, or heat-sensitive/reactive) fiber. Such reactive fibers can be made from polymers having reactive side chains such as amines, sulfonic acid, carboxylic acid, or other functional groups of side chains. Such side chains can be derived from the polymer itself. For example, a polyamine can be formed with a highly functional polyamine leaving acid and amine and mean functionality on the polymer side chains of substituents. Similarly, polysulfone or polyacrylic acid material can be formed having active or reactive acid groups. Similarly, ion exchange resin materials can be made having, within the resin particulate, acid, strongly acid, basic, or strongly basic functional groups that can add absorbent or reactive properties to the invention. Such materials can be dissolved or suspended and can be spun with the conventional fibers of the invention, or can be spun separately into the particle containing webs of the invention.

In an embodiment, the particulate has a major dimension of less than about 200 microns, and typically comprises about 0.05 to 100 microns or comprises about 0.1 to 70 microns. In the substantially continuous fine fiber layer, the layer has a layer thickness of about 25 nm to 2 microns, 0.5 to 500 microns, about 1 to 250 microns, or about 2 to 200 microns. In the layer, dispersed in the fiber, is a means comprising a particulate with a particle size of about 0.25 to 200 microns, about 0.5 to 200 microns, about 1 to 200 microns about 10 to 200, or about 25 to 200 microns. The particulate is dispersed throughout the fiber in the layer. The particulate is present in an amount of about 0.1 to 50 vol %, about 0.5 to 50 vol %, about 1 to 50 vol %, about 5 to 50 vol % or about 10 to 50 vol %. The fiber has a diameter of about 10 nm to 1.0 micron, or 0.001 to about 2 microns, 0.001 to about 1 micron, 0.001 to about 0.5 micron and the layer having a fine fiber solidity of about 0.1 to 65%, about 0.5 to 50%; about 1 to 30% and about 1 to 20%. The particulate is available in the layer in amount of about 1 to 1000 gm-m$^{-2}$, about 5 to 200 gm-m$^{-2}$ or about 10 to 100 gm-m$^{-2}$ of the layer.

An embodiment of the invention includes methods of attaching cells, microorganisms, enzymes or other bioactive molecule to a nanofiber or fine fiber structure or substrate of the invention. Functional groups can be incorporated at the outside surface of the nanofibers. These functionalized surfaces can be reacted to bind a peptide, polypeptide, lipid, carbohydrate, polysaccharide, amino acid, nucleotide, nucleic acid, polynucleotide, or other bioactive molecule to the surface of the nanofiber. In an embodiment, the functionalized surfaces of the nanofiber are reacted to bind one or more bioactive molecules. Preferably one or more of the bioactive molecules is a growth factor, carbohydrate, differentiation factor, adhesive protein, or bioactive peptide derived from an adhesive protein. The growth factor can be VEGF, bone morphogenic factor β, EGF, PDGF, NGF, FGF, IGF, or TGF. The differentiation factor can be neurotrophin, CSF, or TGF.

As a result of the high surface to volume ratio of the fibrous structure or substrate of the invention, the amount of bioactive molecules bound to the nanofibrillar surface is significantly higher than the amount of bioactive molecules absorbed to a planar cell culture surface. In an embodiment, the density of bioactive molecules attached to the nanofibrillar growth matrix is 1 fold greater, 2 fold greater, 3 fold greater, 4 fold greater, or 5 fold greater than the density of bioactive molecules attached to a planar cell culture surface. The higher density of bioactive molecules on the nanofibrillar surface enhances the avidity of the interactions between cells and the nanofiber network to promote biological responses.

In an embodiment, the bioactive molecule is an extracellular matrix (ECM) molecule or fragment thereof. The ECM molecule can be naturally occurring or a synthetic peptide derived from a naturally occurring ECM molecule. Examples of ECM molecules include, but are not limited to, fibronectin, fibrinogen, laminin, and tenascin-C. Examples of synthetic ECM derived peptides include, but are not limited to, synthetic peptides comprising RGD (SEQ ID NO: 43) derived from fibronectin (Meiners et al., 2003, *Mol. Neurobiol.*, 27:177-96; Shin et al., 2003, *Biomaterials*, 24:4353-4364), VFDNFVLKIRDTKKQ (SEQ ID NO:44) derived from tenascin-C (Meiners et al., 2003, *Mol. Neurobiol.*, 27:177-96), YIGSR (SEQ ID NO:45) derived from laminin-1 (Meiners et al., 2003, *Mol. Neurobiol.*, 27:177-96; Shin et al., 2003, *Biomaterials*, 24:4353-4364), and IKAVAV (SEQ ID NO:46) derived from laminin-1 (Meiners et al., 2003, *Mol. Neurobiol.*, 27:177-96; Shin et al., 2003, *Biomaterials*, 24:4353-4364).

The bioactive molecules can be adsorbed or covalently attached to the nanofibrillar surface. Cysteines can be introduced at the N-terminal end of the peptides to provide a functional group for attachment to amines on the nanofiber surface and glycines can be added as spacers. Examples of synthetic ECM peptides that can be covalently attached to the nanofibrillar surface include, but are not limited to, CGGRGDSPG (SEQ ID NO:47), CGGIKAVAV (SEQ ID NO:48), CGGDPGYIGSR (SEQ ID NO:49), and CADEGVFDNFVLKIRDTKKQ (SEQ ID NO:50) (Meiners et al., 2003, *Mol. Neurobiol.*, 27:177-96; Shin et al., 2003, *Biomaterials*, 24:4353-4364).

In an embodiment, functional groups are deposited on the outside surface of a nanofiber by plasma deposition. Plasma deposition creates local plasmas at the surface of the nanofiber. The treated surface is then reacted with gaseous molecules, such as allylamine and/or allyl alcohol, in a reaction chamber. In another embodiment, functional groups are introduced onto the surface of the nanofibers during the electrospinning process. Dodecyl amine, dodecyl aldehyde, dodecyl thiol, or dodecyl alcohol can be added to the polymer solution. The polymer solution is than electrospun into nanofibers in which a portion of the added amines, aldehydes, sulphydryl, or alcohol moieties, respectively, are exposed on the outside surface of the nanofibers.

In an embodiment, a cell, microorganism, enzyme, or other bioactive molecule is genetically engineered to express a cellulose binding domain (CBD). The CBD can be derived from a cellulase or cellulosome. Over 200 CBD sequences have been identified and classified into at least 13 families according to amino acid sequence alignment. See, for example, Tomme et al., 1995, *Adv. Microb. Physiol.*, 37:1-81; Tomme et al., 1998, *J. Chromatogr.* B, 715:283-296; and Boraston et al., 2004, *Biochem. J.*, 382:769-781. The CBD can be from bacteria or fungi. CBD amino acid sequences and nucleic acid sequences can be found, for example, in publicly available data bases such as GenBank (www-ncbi-nlm-nih-gov) or Protein Data Bank (PDB; www-rscb.org./pdb). Preferred CBD include, but are not limited to, CBD from *Clostridium thermocellum*, *Clostridum cellulovorans*, *Clostridium cellulolyticum*, *Clostridium stercorarium*, *Cellulomonas fimi*, *Cellvibrio japonicus*, *Cellvibrio maritima*, *Bacillus circulans*, *Streptomyces olivaceovirdism*, *Streptomyces lividans*, *Rinicus communis*, *Abrus precatorius*, *Tachypleus tridentatus*, *Amaranathus caudatus*, *Urtica dioica*, *Aspergillus niger*, *Bacillus cereus*, *Bacillus* sp. 1139, *Pyromyces equi*, *Micromonospora viridfaciens*, *Cladobotryum dendroides*, *Thermoactinomyces vulgaris*, *Geobacillus stearothermophilus*, *Paenibacillus polymyxa*, *Trichoderma reesie*, *Thermobifida fusca*, *Thermotoga maritima*, *Rhodothermus marinus*, *Erwina chrysanthemi*, *Serratia marcescens*, *Acetivibrio cellulolyticus*, *Bacteroides cellulosovens*, *Aspergillis clavatus*, *Neosartoya fischeri*, *Mycobacterium avium*, or *Plasmodium yoelii*. Representative CBD amino acid sequences for each family are shown in Table 1.

TABLE 1

| Family | CBD Sequence | | Species | PDB Code | SEQ ID NO: |
|---|---|---|---|---|---|
| CBD1 | TQSHYGQCGG SGTTCQVLNP | IGYSGPTVCA YYSQCL | *Tricoderma reesei* | 1CBH | 1 |
| CBD2 | ASSGPAGCQV FTANVTVKNT TFSFPSGQQV SGSAVTVRNA TAQFGFNGSH SLNGTPCTVG | LWGVNQWNTG SSAPVDGWTL TQAWSSTVTQ PWNGSIPAGG TGTNAAPTAF | *Cellulomonas fimi* | 1EXG | 2 |

TABLE 1-continued

| Family | CBD Sequence | Species | PDB Code | SEQ ID NO: |
|---|---|---|---|---|
| CBD2 | TGCSVTATRA EEWSDRFNVT YSVSGSSAWT VNLALNGSQT IQASWNANVT GSGSTRTVTP NGSGNTFGVT VMKNGSSTTP AATCAGS | Cellulomonas fimi | 2XBD | 3 |
| CBD2 | TGSCSVSAVR GEEWADRFNV TYSVSGSSSW VVTLGLNGGQ SVQSSWNAAL TGSSGTVTAR PNGSGNSFGV TFYKNGSSAT PGATCATG | Cellulomonas fimi | 1HEH | 4 |
| CBD3 | AGTGVVSVQF NNGSSPASSN SIYARFKVTN TSGSPINLAD LKRRYYYTQD ADKPLTFWCD HAGYMSGSNY IDATSKVTGS FKAVSPAVTN ADHYLEVALN SDAGSLPAGG SIEIQTRFAR NDWSNFDQSN DWSYTAAGSY MDWQKISAFV GGTLAYGSTP | Clostridium cellulolyticum | 1G43 | 5 |
| CBD3 | NLKVEFYNSN PSDTTNSINP QFKVTNTGSS AIDLSKLTLR YYYTVDGQKD QTFWCDHAAI IGSNGSYNGI TSNVKGTFVK MSSSTNNADT YLEISFTGGT LEPGAHVQIQ GRFAKNDWSN YTQSNDYSFK SASQFVEWDQ VTAYLNGVLV WGKEP | Clostridium thermocellum | 1NBC | 6 |
| CBD3 | EPAFNYAEAL QKSMFFYEAQ RSGKLPENNR VSWRGDSGLN DGADVGLDLT GGWYDAGDHV KFGFPMAFTA TMLAWGAIES PEGYIRSGQM PYLKDNLRWV NDYFIKAHPS PNVLYVQVGD GDADHKWWGP AEVMPMERPS FKVDPSCPGS DVAABTAAAM AASSIVFADD DPAYAATLVQ HAKQLYTFAD TYRGVYSDCV PAGAFYNSWS GYQDELVWGA YWLYKATGDD SYLAKAEYEY DFLSTEQQTD LRSYRWTIAW DDKSYGTYVL LAKETGKQKY IDDANRWLDY WTVGVNGQRV PYSPGGMAVL DTWGALRYAA NTAFVALVYA KVIDDPVRKQ RYHDPAVRQI NYALGDNPRN SSYVVGFGNN PPRNPHHRTA HGSWTDSIAS PAENRHVLYG ALVGGPGSPN DAYTDDRQDY VANEVATDYN AGFSSALAML VEEYGGTPLA DFPPTEEPDG PEIFVEAQIN TPGTTFTEIK AMIRNQSGWP ARMLDKGTFR YWFTLDEGVD PADITVSSAY NQCATPEDVH HVSGDLYYVE IDCTGEKEFP GGQSEHRREV QFRIAGGPGW DPSNDWSFQG IGNELAPAPY IVLYDDGVPV WGTAP | Thermobifida fusca | 1TF4 | 7 |
| CBD4 | SINNGTFDEP IVNDQANNPD EWFIWQAGDY GISGARVSDY GVRDGYAYIT IADPGTDTWH IQFNQWIGLY RGKTYTISFK AKADTPRPIN VKILQNHDPW TNYFAQTVNL TADWQTFTFT YTHPDDADEV VQISFELGEG TATTIYFDDV TVSPQ | Thermotoga maritima | 1GUI | 8 |

TABLE 1-continued

| Family | CBD Sequence | Species | PDB Code | SEQ ID NO: |
|---|---|---|---|---|
| CBD4 | ASPIGEGTFD DGPEGWVAYG TDGPLDTSTG ALCVAVPAGS AQYGVGVVLN GVAIEEGTTY TLRYTATAST DVTVRALVGQ NGAPYGTVLD TSPALTSEPR QVTETFTASA TYPATPAADD PEGQIAFQLG GFSADAWTLC LDDVALDSEV EL; | Cellulomonas fimi | 1ULO; | 9 |
| CBD4 | ASPIGEGTFD DGPEGWVAYG TDGPLDTSTG ALCVAVPAGS AQYGVGVVLN GVAIEEGTTY TLRYTATAST DVTVRALVGQ NGAPYGTVLD TSPALTSEPR QVTETFTASA TYPATPAADD PEGQIAFQLG GFSADAWTLC LDDVALDSE | Cellulomonas fimi | 1GU3 | 10 |
| CBD4 | ASLDSEVELL PHTSFAESLG PWSLYGTSEP VFADGRMCVD LPGGQGNPWD AGLVYNGVPV GEGESYVLSF TASATPDMPV RVLVGEGGGA YRTAFEQGSA PLTGEPATRE YAFTSNLTFP PDGDAPGQVA PHLGKAGAYE FCISQVSLTT SAT | Rhodothermus marinus | 1CX1 | 11 |
| CBD4 | MLVANINGGF ESTPAGVVTD LAEGVEGWDL NVGSSVTNPP VFEVLETSDA PEGNKVLAVT VNGVGNNPWD IEATAFPVNV RPGVTYTYTI WARAEQDGAV VSFTVGNQSF QEYGRLHEQQ ITTEWQPFTF EFTVSDQETV IRAPIHFGYA ANVGNTIYID GLAIASQP | Erwinia chiysanthemi | 1K45 | 12 |
| CBD5 | MGDCANANVY PNWVSKDWAG GQPTHNEAGQ SIVYKGNLYT ANWYTASVPG SDSSWTQVGS CN | Eriwinia chrysanthemi | 1AIW | 13 |
| CBD5 | MSTRKAVIGY YFIPTNQINN YTETDTSVVP PPVSNITPAK AKQLTHINFS FLDINSNLEC AWDPATNDAK ARDVVNRLTA LKAHNPSLRI MFSIGGWYYS NDLGVSHANY VNAVKTPASR AKFAQSCVRI MKDYGFDGVD IDWEYPQAAE VDGFIAALQE IRTLLNQQTI TDGRQALPYQ LTIAGAGGAF FLSRYYSKLA QIVAPLDYIN LMTYDLAGPW EKVTNHQAAL FGDAAGPTFY NALREANLGW SWEELTRAFP SPFSLTVDAA VQQHLMMEGV PSAKIVMGVP FYGPAFKGVS GGNGGQYSSH STPGEDPYPS TDYWLVGCEE CVRDKDPRIA SYRQLEQMLQ GNYGYQRLWN DKTKTPYLYH AQNGLFVTYD DAESFKYKAK YIKQQQLGGV MFWHLGQDNR NGDLLAALDR YFNAADYDDS QLDMGTGLRY TGVGPGNLPI MTAPAYVPGT TYAQGALVSY QGYVWQTKWG YITSAPGSDS AWLKVGRVA | Serratia marcescens | 1E15 | 14 |
| CBD6 | RSAFSKIESE EYNSLKSSTI QTIGTSDGGS GIGYIESGDY LVFNKINFGN GANSFKARVA SGADTPTNIQ LRLGSPTGTL IGTLTVASTG GWNNYEEKSC SITNTTGQHD LYLVFSGPVN IDYFIFDSNG VNP | Clostridium thermocellum | 1UXX | 15 |

TABLE 1-continued

| Family | CBD Sequence | Species | PDB Code | SEQ ID NO: |
|---|---|---|---|---|
| CBD6 | MGSSHHHHHH SSGLVPRGSH MASTPANVNS GPTSPVGGTR SAFSNIQAED YDSSYGPNLQ IFSLPGGGSA IGYIENGYST TYKNIDFGDG ATSVTARVAT QNATTIQVRL GSPSGTLLGT IYVGSTGSFD TYRDVSATIS NTAGVKDIVL VFSGPVNVDW FVFSKSGT | Clostridium stercorarium | 1NAE | 16 |
| CBD6 | GSHMASPTPA PSQSPIRRDA FSIIEAEEYN STNSSTLQVI GTPNNGRGTG YIENGNTVTY SNIDFGSGAT GFSATVATEV NTSIQIRSDS PTGTLLGTLY VSSTGSWNTY NTVSTNISKI TGVHDIVLVF SGPVNVDNFI FSRSS | Clostridium stercorarium | 1UY4 | 17 |
| CBD6 | MVIATIQAED HSQQSGTQQE TTTDTGGGKN VGYIDAGDWL SYAGTPVNIP SSGSYLIEYR VASQNGGGSL TFEEAGGAPV HGTIAIPATG GWQTWTTIQH TVNLSAGSHQ FGIKANAGGW NLNWIRINKT H | Cellvibrio mixtus | 1UZ0 | 18 |
| CBD9 | MVATAKYGTP VIDGEIDEIW NTTEEIETKA VAMGSLDKNA TAKVRVLWDE NYLYVLAIVK DPVLNKDNSN PWEQDSVEIF IDENNHKTGY YEDDDAQFRV NYMNEQTFGT GGSPARFKTA VKLIEGGYIV EAAIKWKTIK PTPNTVIGFN IQVNDANEKG QRVGIISWSD PTNNSWRDPS KFGNLRLIK | Thermotoga martimia | 1I8A | 19 |
| CBD10 | MGNQQCNWYG TLYPLCVTTT NGWGWEDQRS CIARSTCAAQ PAPFGIVGSG | Cellvibrio japonicus | 1QLD | 20 |
| CBD12 | AWQVNTAYTA GQLVTYNGKT YKCLQPHTSL AGWEPSNVPA LWQLQ | Bacillus circulans | 1ED7 | 21 |
| CBD13 | AESTLGAAAA QSGRYFGTAI ASGKLGDSAY TTTASREFNN VTAENEMKID ATEPQRGQFN FSAGDRVYNW AVQNGKQVRG HTLAWHSQQF GWMQSLSGST LRQANIDNIN GVMGHYKGKI AQWDVVNEAF SDDGSGGRRD SNLQRTGNDW IEVAFRTARA ADPAAKLCYN DYNIENWTWA KTQGVYNMVR DFKQRGVPID CVGFQSHFNS GSPYNSNFRT TLQNFAALGV DVAITELDIQ GASSSTYAAV TNDCIAVSRC LGITVWGVRD TDSWRSGDTP LLFNGDGSKK AAYTAVLNAL NGGSSTPPPS GGGQIKGVGS GRCLDVPNAS TTDGTQVQLY DCHSATNQQW TYTDAGELRV YGDKCLDAAG TGNGTKVQIY SCWGGDNQKW RLNSDGSLVG VQSGLCLDAV GGGTANGTLI QLYSCSNGSN QRWTRT | Streptomyces olivacevirdis | 1XYF | 22 |
| CBD13 | EPPADGGQIK GVGSGRCLDV PDASTSDGTQ LQLWDCHSGT NQQWAATDAG ELRVYGDKCL DAAGTSNGSK VQIYSCWGGD NQKWRLMSDG SVVGVQSGLC LDAVGNGTAN GTLIQLYTCS NGSNQRWTRT | Streptomyces lividans | 1MC9 | 23 |

TABLE 1-continued

| Family | CBD Sequence | Species | PDB Code | SEQ ID NO: |
|---|---|---|---|---|
| CBD13 | IFPKQYPIIN FTTAGATVQS YTNFIRAVRG RLTTGADVRH EIPVLPNRVG LPINQRFILV ELSNHAELSV TLALDVTNAY VVGYRAGNSA YFFHPDNQED AEAITHLFTD VQNRYTFAFG GNYDRLEQLA GNLRENIELG NGPLEEAISA LYYYSTGGTQ LPTLARSFII CIQMISEAAR FQYIEGEMRT RIRYNRRSAP DPSVITLENS WGRLSTAIQE SNQGAFASPI QLQRRNGSKF SVYDVSILIP IIALMVYRCA PPPSSQF | Ricinus communis | 2AAI | 24 |
| CBD13 | EDRPIKFSTE GATSQSYKQF IEALRERLRG GLIHDIPVLP DPTTLQERNR YITVELSNSD TESIEVGIDV TNAYVVAYRA GTQSYFLRDA PSSASDYLFT GTDQHSLPFY GTYGDLERWA HQSRQQIPLG LQALTHGISF FRSGGNDNEE KARTLIVIIQ MVAEAARFRY ISNRVRVSIQ TGTAFQPDAA MISLENNWDN LSRGVQESVQ DTFPNQVTLT NIRNEPVIVD SLSHPTVAVL ALMLFVCNPP N | Abrus precatorius | 1ABR | 25 |
| CBD14 | YLAFRCGRYS PCLDDGPNVN LYSCCSFYNC HKCLARLENC PKGLHYNAYL KVCDWPSKAG CTSVNKECHL WKTX | Tachpleus tridenatus | 1DQC | 26 |
| CBD15 | GNVVIEVDMA NGWRGNASGS TSHSGITYSA DGVTFAALGD GVGAVFDIAR PTTLEDAVIA MVVNVSAEFK ASEANLQIFA QLKEDWSKGE WDCLAGSSEL TADTDLTLTC TIDEDDDKFN QTARDVQVGI QAKGTPAGTI TIKSVTITLA QEA | Cellvibrio japonicus | 1GNY | 27 |
| CBD17 | QPTAPKDFSS GFWDFNDGTT QGFGVNPDSP ITAINVENAN NALKISNLNS KGSNDLSEGN FWANVRISAD IWGQSINIYG DTKLTMDVIA PTPVNVSIAA IPQSSTHGWG NPTRAIRVWT NNFVAQTDGT YKATLTISTN DSPNFNTIAT DAADSVVTNM ILFVGSNSDN ISLDNIKFTK | Clostridium cellulovorans | 1J83 | 28 |
| CBD18 | ERCGEQGSNM ECPNNLCCSQ YGYCGMGGDY CGKGCQNGAC NTSKRCGSQA GGATCTNNQC CSQYGYCGFG AEYCGAGCQG GPCRADIKCG SQAGGKLCPN NLCCSQWGFC GLGSEFCGGG CQSGACSTDK PCGKDAGGRV CTNNYCCSKW GSCGIGPGYC GAGCQSGGCD G | Triticum aestivum | 1WGC | 29 |
| CBD18 | VGECVRGRCP SGMCCSQFGY CGKGPKYCGR | Amaranthus caudatus | 1MMC | 30 |
| CBD18 | ERCGSQGGGS TCPGLRCCSI WGWCGDSEPY CGRTCENKCW SGERSDHRCG AAVGNPPCGQ DRCCSVHGWC GGGNDYCSGG NCQYRCSSS | Urtica dioica | IBIS | 31 |

TABLE 1-continued

| Family | CBD Sequence | Species | PDB Code | SEQ ID NO: |
|---|---|---|---|---|
| CBD20 | CTTPTAVAVT FDLTATTTYG ENIYLVGSIS QLGDWETSDG IALSADKYTS SDPLWYVTVT LPAGESFEYK FIRIESDDSV EWESDPNREY TVPQACGTST ATVTDTWR | Aspergillus niger | 1AC0 | 32 |
| CBD20 | TPVMQTIVVK NVPTTIGDTV YITGNPAELG SWDTKQYPIQ LYYDSHSNDW RGNVVLPAER NIEFKAFIKS KDGTVKSWQT IQQSWNPVPL KTTSHTSSW | Bacillis cereus | 1CQY | 33 |
| CBD22 | KPEEPDAGYY YHDTFEGSVG QWTARGPAEV LLSGRTAYKG SESLLVRNRT AAWNGAQRAL NPRTFVPGNT YCFSVVASFI EGASSTTFCM KLQYVDGSGT QRYDTIDMKT VGPNQWVHLY WPQYRIPSDA TDMYVYVETA DDTINFYIDE AIGAVAGTVI | Clostridium thermocellum | 1DYO | 34 |
| CBD27 | MASNEARYVL AEEVDFSSPE EVKNWWNSGT WQAEFGSPDI EWNGEVGNGA LQLNVKLPGK SDWEEVRVAR KFERLSECEI LEYDIYIPNV EGLKGRLRPY AVLNPGWVKI GLDMNNANVE SAEIITFGGK EYRRFHVRIE FDRTAGVKEL HIGWGDHLR YDGPIFIDNV RLYKRTGGM | Thermotoga maritime | 1OF4 | 35 |
| CBD28 | GTEVEIPVVH DPKGEAVLPS VFEDGTRQGW DWAGESGVKT ALTIEEANGS NALSWEFGYP EVKPSDNWAT APRLDFWKSD LVRGENDYVT FDFYLDPVRA TEGAMNINLV FQPPTNGYWV QAPKTYTINF DELEEANQVN CLYHYEVKIN VRDITNIQDD TLLRNMMIIF ADVESDFAGR VFVDNVRFEG A | Bacillus sp. 1139 | 1UWW | 36 |
| CBD29 | MNVRATYTVI FKNASGLPNG YDNWGWGCTL SYYGGAMIIN PQEGKYGAVS LKRNSGSFRG GSLRFDMKNE GKVKILVENS EADEKFEVET ISPSDEYVTY ILDVDFDLPF DRIDFQDAPG NGDRIWIKNL VHSTGSADDF VDPINLEHHH HNH | Pyromyces equi | 1GWK | 37 |
| CBD32 | VPPGEPLYT EQDLAVNGRE GFPNYRIPAL TVTPDGDLLA SYDGRPTGID APGPNSILQR RSTDGGRTWG EQQVVSAGQT TAPIKGFSDP SYLVDRETGT IFNFEVYSQR QGFAGSRPGT DPADPNVLHA NVATSTDGGL TWSHRTITAD ITPDPGWRSR FAASGEGIQL RYGPHAGRLI QQYTIINAAG AFQAVSVYSD DHGRTWRAGE AVGVGMDENK TVELSDGRVL LNSRDSARSG YRKVAVSTDG GHSYGPVTID RDLPDPTNNA SIIRAFPDAP AGSAPAKVLL FSNAASQTSR SQGTIRMSCD DGQTWPVSKV FQPGSMSYST LTALPDGTYG LLYEPGTGIR YANFNLAWLG GICAPFTIPD VALEPGQQVT VPVAVTNQSG IAVPKPSLQL DASPDWQVQG SVEPLMPGRQ AKGQVTITVP AGTTPGRYRV GATLRTSAGN ASTTFTVTVG LLDQARMSIA DVDSEETARE DGRASNVIDG NPSTFWHTEW SRADAPGYPH | Micromonospora viridifaciens | 1EUU | 38 |

TABLE 1-continued

| Family | CBD Sequence | Species | PDB Code | SEQ ID NO: |
|---|---|---|---|---|
| | RISLDLGGTH TISGLQYTRR<br>QNSANEQVAD YEIYTSLNGT<br>TWDGPVASGR FTTSLAPQRA<br>VFPARDARYI RLVALSEQTG<br>HKYAAVAELE VEGQR | | | |
| CBD32 | ASAPIGSAIS RNNWAVTCDS<br>AQSGNECNKA IDGNKDTFWH<br>TFYGANGDPK PPHTYTIDMK<br>TTQNVNGLSM LPRQDGNQNG<br>WIGRHEVYLS SDGTNWGSPV<br>ASGSWFADST TKYSNFETRP<br>ARYVRLVAIT EANGQPWTSI<br>AEINVFQASS YTAPQPGLGR<br>WGPTIDLPIV PAAAAIEPTS<br>GRVLMWSSYR NDAFGGSPGG<br>ITLTSSWDPS TGIVSDRTVT<br>VTKHDMFCPG ISMDGNGQIV<br>VTGGNDAkKT SLYDSSSDSW<br>IPGPDMQVAR GYQSSATMSD<br>GRVFTIGGSW SGGVFEKNGE<br>VYSPSSKTWT SLPNAKVNPM<br>LTADKQGLYR SDNHAWLFGW<br>KKGSVFQAGP STANNWYYTS<br>GSGDVKSAGK RQSNRGVAPD<br>AMCGNAVMYD AVKGKILTFG<br>GSPDYQDSDA TTNAHIITLG<br>EPGTSPNTVF ASNGLYFART<br>FHTSVVLPDG STFITGGQRR<br>GIPFEDSTPV FTPEIYVPEQ<br>DTFYKQNPNS IVRVYHSISL<br>LLPDGRVFNG GGGLCGDCTT<br>NHFDAQIFTP NYLYNSNGNL<br>ATRPKITRTS TQSVKVGGRI<br>TISTDSSISK ASLIRYGTAT<br>HTVNTDQRRI PLTLTNNGGN<br>SYSFQVPSDS GVALPGYWML<br>FVMNSAGVPS VASTIRVTQ | *Cladobotryum dendroides* | 1GOF | 39 |
| CBD34 | AANDNNVEWN GLFHDQGPLF<br>DNAPEPTSTQ SVTLKLRTFK<br>GDITSANIKY WDTADNAFHW<br>VPNVWDSNDP TGTFDYWKGT<br>IPASPSIKYY RFQINDGTST<br>AWYNGNGPSS TEPNADDFYI<br>IPNFKTPDWL KNGVMYQIFP<br>DRFYNGDSSN DVQTGSYTYN<br>GTPTEKKAWG SSVYADPGYD<br>NSLVFFGGDL AGIDQKLGY<br>IKKTLGANILY<br>LNPIFKAPTN HKYDTQDYMA<br>VDPAFGDNST<br>LQTLINDIHST ANGPKGYLI<br>LDGVFNHTGD SHPWFDKYNN<br>FSSQGAYESQ SSPWYNYYTF<br>YTWPDSYASF LGFMSLPKLN<br>YGNSGSAVRG VIYNNSNSVA<br>KTYLNPPYSV DGWRLNAAQY<br>VDANGNNGSD VTNHQIWSEF<br>RNAVKGVNSN AAIIGQYWGN<br>ANPWTAQGNQ WDAATNFDGF<br>TQPVSEWITG KDYQNNSASI<br>STTQFDSWLR GTRANYPTNV<br>QQSMMNFLSN HDITRFATRS<br>GGDLWKTYLA LIFQMTYVGT<br>PTIYYGDEYG MQGGADPDNR<br>RSFDWSQATP SNSAVALTQK<br>LITIRNQYPA LRTGSFMTLT<br>TDDTNKIYSY GRFDNVNRIA<br>VVLNNDSVSH TVNPVWQLS<br>MPNGSTVTDK ITGHSYTVQN<br>GNVTVAVDGH YGAVLAQ | *Thermoactinomyces vulgaris* | 1UH2 | 40 |
| CBD34 | MRKEAIYHRP ADNFAYAYDS<br>ETLHLRLRTK KDDIDRVELL<br>HGDPYDWQNG AWQFQMMPMR<br>KTGSDELFDY WFAEVKPPYR<br>RLRYGFVLYS GEEKLVYTEK | *Geobacillus stearothermophilus* | 1JOH | 41 |

TABLE 1-continued

| Family | CBD Sequence | | Species | PDB Code | SEQ ID NO: |
|---|---|---|---|---|---|
| | GFYFEVPTDD | TAYYFCFPFL | | | |
| | HRVDLFEAPD | WVKDTVWYQI | | | |
| | FPERFANGNP | SISPEGSRPW | | | |
| | GSEDPTPTSF | FGGDLQGIID | | | |
| | HLDYLVDLGI | TGIYLTPIFR | | | |
| | SPSNHKYDTA | DYFEVDPHFG | | | |
| | DKETLKTLID | RCHEKGIRVM | | | |
| | LDAVFNHCGY | EFAPFQDVWK | | | |
| | NGESSKYKDW | FHIHEFPLQT | | | |
| | EPRPNYDTFA | FVPQMPKLNT | | | |
| | ANPEVKRYLL | DVATYWIREF | | | |
| | DIDGWRLDVA | NEIDHEFWRE | | | |
| | FRQEVKALKP | DVYILGEIWH | | | |
| | DAM WLRGDQ | FDAVMMYPFT | | | |
| | DGVLRFFAKE | EISARQFANQ | | | |
| | MMHVLHSYPN | NVNEAAFNLL | | | |
| | GSHDTSRILT | VCGGDIRKVK | | | |
| | LLFLFQLTFT | GSPCIYYGDE | | | |
| | IGMTGGNDPE | CRKCMVWDPM | | | |
| | QQNKELHQHV | KQLIALRKQY | | | |
| | RSLRRGEISF | LHADDEMNYL | | | |
| | IYKKTDGDET | VLVIINRSDQ | | | |
| | KADIPIPLDA | RGTWLVNLLT | | | |
| | GERFAABAET | LCTSLPPYGF | | | |
| | VLYAIEHW | | | | |
| CBD36 | ITKVEAENMK | IGGTYAGKIS | *Paenibacillus* | 1UX7 | 42 |
| | APFDGVALYA | NADYVSYSQY | *polymyxa* | | |
| | FANSTHNISV | RGASSNAGTA | | | |
| | KVDLVIGGVT | VGSFNFTGKT | | | |
| | PTVQTLSNIT | HATGDQEIKL | | | |
| | ALTSDDGTWD | AYVDFIEFSL | | | |

CBD amino acid sequences can be identified by aligning the sequences with one or more of the reference sequences shown in Table 1 and determining the percent amino acid sequence identity to the reference amino acid sequence. "Percent (%) amino acid sequence identity" means the percentage of amino acid residues in a polypeptide that are identical with amino acids in a reference polypeptide, after aligning the sequence and introducing gaps, if necessary to achieve the maximum sequence identity, and not considering any conservative substitutions as part of the sequence identity. For purposes herein, the % amino acid sequence identity of a given amino acid sequence A to, with, or against a given amino acid sequence B (which can alternatively be phrased as a given amino acid sequence A that has or includes a certain % amino acid sequence identity to, with, or against a given amino acid sequence B) is calculated as follows:

100 times the fraction X/Y where X is the number of amino acid residues scored as identical matches by the sequence alignment, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The % amino acid sequence identity can also be determined using the sequence comparison program such as ALIGN 2 or NCBI-BLAST2 (Altschul et al., 1997, *Nucleic Acids Res.*, 25:3389-3402). The NCBI-BLAST2 sequence comparison program can be downloaded from http://www-ncbi-nlm-nih-gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The CBD can include deletions and additions of amino acids, as well as amino acid substitutions. Variants of naturally occurring CBD described herein, can be made, for example, using any of the techniques and guidelines for conservative and non-conservative mutations set forth, for example, in U.S. Pat. No. 5,364,934.

The sequences of the CBD can be compared and aligned to other known CBD sequences and locations of amino acid positions for substitutions can be identified as those positions that show a high degree of variability in amino acids, i.e. at least 3 different amino acids are found at that position when different sequences are aligned and compared or have a lower percentage of sequence identity i.e. less than 90% sequence identity. When sequences are aligned, the positions that show variability can either have conservative amino acid substitutions or non-conservative amino acid substitutions. If the position has conservative amino acid substitutions, that would indicate that the amino acid substituted at that position should be of the same type as those observed to be at that position in naturally occurring proteins. For examples of such substitutions, see Table 2. In particular embodiments, conservative substitutions of interest are shown in Table 2 under the heading of preferred substitutions.

TABLE 2

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |

TABLE 2-continued

| Original Residue | Exemplary Substitutions | Preferred Substitutions |
|---|---|---|
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; type | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Amino acid substitutions can be the result of replacing one amino acid with another amino acid having similar structural and/or chemical properties, such as the replacement of a leucine with a serine, i.e., conservative amino acid replacements. Insertions or deletions can optionally be in the range of about 1 to 5 amino acids. The variation allowed can be determined by systematically making insertions, deletions or substitutions of amino acids in the sequence and testing the resulting variants for activity exhibited by the full-length or mature naturally occurring sequence. Preferably, variants have a biological activity of the source molecule, such as for example, cellulose binding activity.

The variations can be made using methods known in the art such as oligonucleotide-mediated (site-directed) mutagenesis, alanine scanning, and PCR mutagenesis. Site-directed mutagenesis (Carter et al., 1986, *Nucl. Acids Res.*, 13:4331; Zoller et al., 1987, *Nucl. Acids Res.*, 10:6487), cassette mutagenesis (Wells et al., 1985, *Gene*, 34:315), restriction selection mutagenesis (Wells et al., 1986, *Philos. Trans. R. Soc. London SerA,* 317:415) or other known techniques can be performed on the cloned DNA to produce the chymopapain variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, 1989, *Science,* 244: 1081-1085). Alanine is also typically preferred because it is the most common amino acid. Further, it is frequently found in both buried and exposed positions (Creighton, *The Proteins,* (W.H. Freeman & Co., N.Y.); Chothia, 1976, *J. Mol. Biol.,* 150:1). If alanine substitution does not yield adequate amounts of variant, an isoteric amino acid can be used.

Variant CBD can be generated by any known method for substituting, deleting, or inserting one or more codons that result in a change in the amino acid sequence of CBD as compared with a reference sequence for CBD. In an embodiment, the CBD sequence has at least 80%, 85%, 86%, 87%, 88%, 89%, 90%, 91%, 92%, 93%, 94%, 95%, 96%, 97%, 98%, or 99% amino acid sequence identity to any one of the amino acid sequences shown in Table 1 and binds to cellulose or a cellulose derivative.

Polynucleotide sequences encoding CBD can be synthesized, and/or cloned, and expressed according to techniques well known to those of ordinary skill in the art. See, for example, Sambrook, et al., *Molecular Cloning, A Laboratory Manual,* Vols. 1-3, Cold Spring Harbor Press, Cold Spring Harbor, N.Y. (1989). Polynucleotides encoding CBD can be produced by standard recombinant methods known in the art, such as polymerase chain reaction (Sambrook et al., *Molecular Cloning, A Laboratory Manual,* Vols. 1-3, Cold Spring Harbor Press, Cold Spring Harbor, N.Y. (1989). The peptide constructs can be assembled from polymerase chain reaction cassettes sequentially cloned into a vector containing a selectable marker for propagation in a host. Such markers include dihydrofolate reductase or neomycin resistance for eukaryotic cell culture and tetracycline or ampicillin resistance genes for culturing in *E. coli* and other bacteria.

Bacterial expression vectors can be used to express CBD. Plasmid pET 28a (Novagen, Madison, Wis.) is an example of a suitable expression vector. The nucleotide sequence and map of the pET 28a vector is known and readily available on the internet at www-emdbiosciences-com. Baculovirus expression vectors can be used to express CBD. Many baculovirus expression systems are commercially available, such as Baculogold (Pharmingen), Bac-n-Blue (Invitrogen), Bac Pak (Clontech), and Bac Vector (Novagen, Madison, Wis.).

Representative examples of appropriate hosts include, but are not limited to, bacterial cells such as *E. coli, Streptomyces,* and the microorganisms shown in Table 1, fungal cells, yeast; insect cells such as *Drosophilia* S2 and *Spodoptera* Sf9 or Sf21, animal cells such as CHO, COS, and Bowes melanoma cells, and plant cells. Appropriate culture medium and conditions for the above-described host cells are known in the art.

The polynucleotides of the invention can be operably linked to an appropriate promoter, such as the isopropyl β-D-thiogalactopyranoside (IPTG) inducible T7 promoter in plasmid pET 28a (Studier et al., 1990, *Methods Enzymol.,* 185: 60-89). Other suitable promoters are known in the art. The expression constructs may further contain sites for transcription initiation, transcription termination, and a ribosome binding site for translation. The coding portion of the mature polypeptide expressed by the constructs can include a translation initiating codon at the beginning and a termination codon (UAA, UGA, or UAG) appropriately positioned at the end of the polypeptide to be translated.

Introduction of the recombinant vector into the host cell can be effected by calcium phosphate transfection, DEAE-dextran mediated transfection, cationic lipid-mediated transfection, electroporation, transduction, infection, or other methods. Such methods are described in standard laboratory manuals such as Sambrook, et al., 1989, Molecular Cloning, A Laboratory Manual, Vols. 1-3, Cold Spring Harbor Press, Cold Spring Harbor, N.Y. or Davis et al., 1986, *Basic Methods in Molecular Biology.* Commercial transfection reagents, such as Lipofectamine (Invitrogen, Carlsbad, Calif.) and FuGENE 6™ (Roche Diagnostics, Indianapolis, Ind.), are also available.

Cells or microorganisms expressing CBD bind to nanofibers comprising a cellulosic material or celluosic derivative. In an embodiment, the cellulosic nanofibers comprising the structure or substrate of the invention can be combined with a stabilizing nanofiber. The stabilizing nanofiber comprises nanofibers of polymeric materials, as provided elsewhere in this description. In an embodiment, the nanofiber cellulosic substrate comprises cellulose esters such as cellulose acetate and cellulose triacetate, xylan, pectin, chitin, and other similar polysaccharides. The particulate dispersed within the fiber web or layer of the invention can comprise cellulosic materials and cellulose derivative beads. Such beads can be manufactured from cellulose or from cellulose derivatives such as methyl cellulose, ethyl cellulose, hydroxymethyl cellulose, hydroxyethyl cellulose, and others.

In another embodiment, a phage display library is probed with CBD sequences or various strains of cellulytic bacteria or fungus to identify a specific peptide that binds to the outer surface of the bacteria or fungus or is bound by CBD. The identified peptide is cloned, sequenced, and attached to the nanofibers or fine fiber structure of the invention. The identified peptide provides an anchoring site on the nanofibers for specific strains of cellulytic bacteria of fungus or cells or microorganisms expressing CBD.

Phage display vectors and methods for constructing phage display libraries and probing a phage display library are known. See, for example, Smith and Petrenko, 1997, *Chem. Rev.*, 97:391-410; www-biosci-missouri-edu/smithgp/PhageDisplayWebsite; U.S. Pat. No. 5,270,170; U.S. Pat. No. 5,565,325; WO/0035940; and WO03/56691. Peptide library synthesis kits and screening kits are commercially available, for example, from Novagen (NOVATOPE®; Madison. Wis.) and Sigma-Genosys (The Woodlands, Tex.). Peptide libraries are also commercially available, for example, from Dyax (Cambridge, Mass.) and Princeton BioMolecules Corp. (Langhorne, Pa.).

In an embodiment, peptide is displayed on the surface of a phage as a fusion with one of the coat proteins of the virus. The DNA encoding the peptide is housed within the virion. By cloning large numbers of DNA sequences into the phage, display libraries are produced. Biopanning can be used to rescue phage displaying a peptide that specifically binds to a CBD or a cellulolytic bacteria or fungus. In an embodiment, biopanning comprises coating a solid substrate with the target and incubating the library on the substrate to allow phage displaying a complementary protein to the target to bind. The substrate can be a plate or chip. Non-binding phage are then washed away and those that are bound are eluted. Infection of bacteria with the binding phage results in phage amplification. Successive rounds of biopanning enrich the pool of phage with clones that specifically bind the target. DNA sequencing of the phage genome determines the amino acid sequence of the peptides binding to the target.

In an embodiment, the bioactive particulate is attached or tethered to the fine fiber layer of the multilamellar matrix, through tether molecules or moieties, such as functional groups or molecules on the fine fiber layer that can react with or bind to the cell, microorganism, enzyme, or other bioactive molecule comprising the bioactive particulate. Such functional groups include alcohol, aldehyde, amine, carboxyl, sulphydryl, etc. groups. In aspects, the functional groups on the fiber layer are photoactivable groups, such as carbene or nitrene, for example. In an aspect, the fine fiber layer comprises an adhesion molecule that promotes attachment of the bioactive particulate to the fiber layer. Such adhesion molecules include, for example, fibronectin, laminin, thrombospondin, tenascin C, actin, fibrin, fibrinogen, vitronectin, cadherin, selectin, intracellular adhesion molecules 1, 2, or 3, cell-matrix adhesion receptor, and combinations or mixtures thereof. The cell-matrix adhesion receptor of the invention comprises an integrin, such as $\alpha_5\beta_1$, $\alpha_6\beta_1$, $\alpha_7\beta_1$, $\alpha_1\beta_2$, $\alpha_2\beta_3$, or $\alpha_6\beta_4$, for example. In an aspect, the bioactive particulate comprises a cellulose binding domain that binds to the cellulose or cellulose derivative comprising the fine fiber layer. In an aspect, the functional groups or moieties on the fiber surface can act as tethers that hold the bioactive particulate to the fiber surface, and also provide appropriate spacing or separation between the bioactive particulate and the fiber. The tether moieties may also comprise a spacer particulate between fiber layers of the multilamellar matrix. The spacer has a thickness and a first and second surface. The first surface of the spacer contacts the surface of a first fiber layer, while the second surface of the spacer contacts the surface of a second fiber layer, the first and second fiber layers being separated by the thickness of the spacer.

The nanofiber webs and fine fiber structures of the invention can be used as a culture and/or growth surface in a bioreactor or fermentation device to produce high value pharmaceutical or biologics, such as recombinant polypeptides or antibodies having therapeutic activity. The antibodies can be monoclonal. The monoclonal antibodies can be chimeric or humanized. Cells or microorganisms that have been genetically engineered to produce antibodies can be grown in a nanofiber web or fine fiber structure of the invention as described herein. The cells or microorganisms can be tethered to the nanofiber web or structure as described herein.

Many bioreactor and fermentation devices and techniques are known for producing proteins recombinantly using a variety of host cell systems including *E. coli*, yeast, plant cells, insect cells, and mammalian cells. See, for example, U.S. 20040229310; U.S. 20040229310, Yang et al., 2004, *Adv. Biochem. Eng. Biotechnol.*, 87:61-96; Farid, 2006, *Adv. Biochem. Eng. Biotechnol.*, 101:1-42; Doran, Bioprocess Engineering Principles, 2nd Ed., Acad. Press (San Diego, Calif.), 1995. A variety of solid state fermentation devices have previously been described. For a review see, for example, Laroche et al., 1997, *Adv. Biochem. Eng. Biotechnol.*, 55:179; Roussos et al., 1993, *Appl. Biochem. Biotechnol.*, 42:37-52; Smits et al., 1998, Agro-Food-Industry Hi-Tech, March/April: 29-36 Eukaryotic and prokaryotic systems can be used in large-scale production of antibodies. Host cells and vectors for producing antibodies are known. In an embodiment, the host cells comprise CHO cells or *E. coli*.

In one aspect of the invention, the antibody production or recombinant polypeptide production is conducted in large quantity by a fermentation process. Various large-scale fed-batch fermentation procedures are available for production of recombinant proteins. Large-scale fermentations have at least 10 liters of capacity, preferably about 100 to 100,000 liters of capacity. These fermentors use agitator impellers to distribute oxygen and nutrients, especially glucose (the preferred carbon/energy source). Small-scale fermentation refers generally to fermentation in a fermentor that is no more than approximately 9 liters in volumetric capacity, and can range from about 1 liter to about 9 liters.

In a fermentation process, induction of protein expression is typically initiated after the cells have been grown under suitable conditions to a desired density, e.g., an $OD_{550}$ of about 1.80-2.20, at which stage the cells are in the early stationary phase. A variety of inducers may be used, according to the vector construct employed, as is known in the art. Cells may be grown for shorter periods prior to induction. Cells are usually induced for about 12-50 hours, although longer or shorter induction time maybe used.

To improve the production yield and quality of the antibodies or recombinant polypeptides, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and/or OsbG) or FkpA (a peptidylprolyl cis, trans-isomerase with chaperone activity) can be used to co-transform host prokaryotic cells. The chaperone proteins have been demonstrated to facilitate the proper folding and solubility of heterologous proteins produced in bacterial host cells. Chen et al., 1999, *J. Biol. Chem.* 274:19601-19605; U.S. Pat. No. 6,083, 715; U.S. Pat. No. 6,027,888; Botbmano and Pluckthun, 2000, *J. Biol. Chem.* 275:17100-17105; Ramm and Pluckthun, 2000, *J. Biol. Chem.* 275:17106-17113; Arie et al., 2001, *Mol. Microbiol.* 39:199-210.

To minimize proteolysis of expressed heterologous proteins (especially those that are proteolytically sensitive), certain prokaryotic host strains deficient for proteolytic enzymes can be used for the present invention. For example, host cell strains can be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al., 1998, supra; U.S. Pat. No. 5,264,365; U.S. Pat. No. 5,508,192; Hara et al., 1996, *Microbiol. Drug Resistance*, 2:63-72.

Another aspect of the invention includes methods of processing biomass. Methods for the conversion of biomass to alcohol are provided. In an embodiment, cellulosic biomass is converted into ethanol or butanol by fermentation in a bioreactor system. Briefly, the growth media or culture media of the invention is cultured with a microorganism capable of enzymatically digesting cellulose, pectin, starch, xylan or mixtures thereof. The growth media is then contacted with the cellulosic biomass under conditions that promote microbial fermentation. During fermentation, the microorganism anaerobically reduces pyruvate to $NAD^+$, producing alcohols such as ethanol or butanol as metabolic byproducts. In another aspect, the nanofiber webs and fine fiber structures or substrates of the invention can be used as a culture and/or growth surface to form biofilms during bioprocessing or bioconversion. Biofilm formation is a natural process where microorganisms can attach to a support or adsorbent to form thick layers of cells (i.e. the biofilm), and is further described in Qureshi et al., *Microbial Cell Factories* 2005, 4: 24-45. Biofilm formation increases cell density and concentration in the bioreactor, and thereby increases the reaction rate and subsequent yield of ethanol or butanol. Biofilm formation is also useful in biological wastewater treatment. The biofilm helps convert ammonia in wastewater streams to nitrogen gas through a simultaneous nitrification and denitrification process. Biological contaminates in wastewater streams can be removed by first culturing a microorganism capable of forming a biofilm with the growth or culture media of the bioreactor. The biomass (comprising solids and wastewater) is then contacted with the cultured growth media. The biofilm allows oxygen to penetrate into the bioreactor creating a gradient of oxygen and providing aerobic denitrification of the wastewater.

Microorganisms capable of biofilm formation or fermenting cellulosic biomass include various types of yeast and anaerobic bacteria, such as, for example, species of *Saccharomyces, Clostridium, Thermoanaerobacterium*, certain species of *Eubacterium, Zymomonas*, and others. Certain types of filamentous fungi can also be used for this process, including species of *Monilia, Neurospora, Aspergillus, Zygosaccharomyces, Trichoderma*, and *Paecilomyces*. In embodiments, the fermentation process with the bioreactor growth media of the invention uses a species of *Saccharomyces*, including *S. cerevisae, S. pastorianus, S. uvarum, S. bayanus*, or hybrids of these species. Species of *Clostridium* useful for the methods of the invention include *C. phytofermentans, C. thermocellum, C. cellulolyticum, C. acetobutylicum, C. populeti, C. polysaccharolyticum, C. herbivorans, C. lentocellum, C. celerecrescens, C aminovalericum, C. butyricum, C. beijerinckii, C. cellulovorans, C. xylanovorans, C. xylanolyticum*, and hybrids thereof. Other microorganisms that are used in the fermentation methods of the invention include *T. thermosaccharolyticum, E. xylanophilum, E. cellulosolvens, Z. mobilis*, etc.

In yet another aspect, the present invention provides methods for consolidated bioprocessing (CBP) of cellulosic biomass. The conversion of biomass to ethanol commonly involves four transformations: the production of saccharolytic enzymes (i.e. cellulase and hemicellulase), the hydrolysis of carbohydrate components to sugars; the fermentation of hexose sugars (glucose, mannose, galactose), and the fermentation of pentose sugars (xylose, arabinose). In consolidated bioprocessing, the various transformations required for enzymatic or microbial conversion of biomass to alcohol are conducted in a single step. CBP methods have the potential for lower costs and higher efficiency relative to multistep methods.

In the CBP methods of the invention, a first surface of the growth media is contacted with the cellulosic biomass. In an embodiment, this first surface includes a fine fiber layer in which a bioactive particulate has been dispersed. The bioactive particulate comprises an enzyme, such as cellulase, hemicellulase, cellulosome, for example. Such enzymes are capable of converting cellulose, cellulose derivatives and other polysaccharides such as pectin, starch, xylan, etc. to hexose and pentose sugars. A second surface of the growth media is then contacted with the pentose and hexose sugars. This second surface comprises a bioactive particulate that promotes microbial fermentation, and thereby converts the sugars into ethanol. Microorganisms capable of microbial fermentation include various types of yeast and anaerobic bacteria, such as, for example, species of *Saccharomyces, Clostridium, Thermoanaerobacterium*, certain species of *Eubacterium, Zymomonas*, and others.

In one aspect, the nanofiber webs and fine fiber structures or substrates of the invention can be used as part of a device for simulating an organ's functions, i.e. a bioartificial organ, such as a bioartificial kidney, for example. The web of the invention comprises a culture or growth surface for cell attachment and proliferation. For example, normal kidney fibroblasts can be cultured on the growth media or web of the invention, using nanofibers electrospun from a solution comprising 10% polycaprolactone (w/w) in chloroform supplemented with 0.25% sphingomyelin in Dulbecco Modified Eagle's Medium (DME) at 37° C. in 5% $CO_2$. These kidney cells bound to the fiber web or substrate act as ion pumps and reabsorb vital electrolytes, water and glucose filtered out of blood during hemofiltration, in addition to producing other important molecules necessary for proper kidney function and normal fluid maintenance. In an embodiment, the normal kidney fibroblasts are human or porcine.

In another aspect, the web comprises a continuous fibrous structure with a continuous fiber phase and a bioactive, reactive, absorptive, or adsorptive active particulate that can treat a fluid stream, by removing chemicals and/or entrained materials. The fluid stream can be a liquid with entrained materials or dissolved chemicals. The entrained materials can be soluble or insoluble in the mobile fluids and can be particulates of liquid impurities, solid impurities, and biological contaminates, including harmful biological products that can cause cytotoxicity, inhibit peptide synthesis, etc. Such impurities can be entrained particulates. The liquids can be exemplified by aqueous solutions, nonaqueous fluids, water, oils, and mixtures thereof. The flow-through and flow-by structures can be used in structures that need no PTFE, stretched expanded Teflon® or other related porous fluoropolymer components for successful activity.

By dispersed is meant that the active particulate is adhered to the fiber, held within a void space within the web, or in a pocket penetrating partially into the web creating a space in the web surface. Once formed, the media comprising the fine fiber layer containing the active particulate of the invention can be combined with a media layer. That form can be used in a flow-by treatment unit or used in a flow-through filtration unit having adsorptive/absorptive or bioactive properties. In a flow-by or pass-through unit, the media is simply configured in a form through which the mobile fluid can pass unimpeded by any filtration layer and simply contact the absorptive/adsorptive or reactive species formed in the fine fiber layer adjacent to the flow path of the fluid media. Alternatively, the fine fiber layer containing the active particulate and media can be formed in a flow-through filtration structure that can remove particulate from the mobile fluid while in the infiltration mode, the media of the invention can, in a filtration mode, remove the entrained particulate from mobile fluid and at the same time absorb, adsorb or chemically react with unwanted materials in the fluid phase that may or may not be in a particulate form.

The term filter refers to the structure that is actually used in treating a mobile fluid. A "filter" usually includes a housing with an inlet and outlet. The term "element" typically refers to a structure used in a filter assembly that includes a media layer and other parts resulting in a useful structurally stable unit that can be inserted and removed from the filter structure. Elements or webs of the invention include media layer that comprises a particulate dispersed throughout a fine fiber web. The combined fine fiber and particulate can be formed on a substrate layer to form a filter medium.

The particulate can comprise an amount of a single type of particulate or blend of dissimilar particles. For example, an active particulate can be blended with an inert particulate for use in such a layer. The inert particulate can comprise a single particulate or can be a blend of inert particulate that differs by composition particle size, particle morphology or some other particle aspect. Similarly, the active particulate can comprise a mixture of particulates including different active particulates. For example, a carbon particulate could be blended with a zeolite particulate. Alternatively, a carboxy methyl cellulose particulate can be blended with an ion exchange resin particulate in an active layer. Further, such active particulate can have a blended particulate in the sense that particulates of different size, shape or methodology can be combined in the active layers of the invention. The term "entrained particulate" refers to impurities in the mobile fluid while the term "dispersed particulate" refers to the particulate deliberately included within the fiber layers of the invention.

The element of the invention can be used in one of two separate modes. These modes are designated as "flow-through" or "flow-by". In the flow-through mode, the mobile fluid, liquid or gas, passes through the fine fiber layer and substrate in a filtration mode in a flow substantially normal to the plane of the fiber layer. The entrained particulate can encounter and be removed by the element and as the fluid passes through the layers in contact with the particulate, the particulate can react with absorbed or adsorbed chemical materials suspended or dissolved in the fluid.

In the flow-by mode, the fluid path is generally parallel to the plane of the fine fiber layer or element surface. In the flow-by mode, the fluid contacts the surface of the layer and does not substantially flow through the element. While depending on viscosity, flow rate, temperature, element configuration, the fluid can to some degree penetrate the layer and can flow from layer to layer, the primary mode of transport of the fluid is bypassing the layer in a direction substantially parallel to the layer's surface. In such a mode, the liquid can contact the surface of the layer and chemical materials dissolved and suspended in the fluid can react with, be absorbed, or adsorbed by the particulate.

The flow-through and flow-by element can be used in a variety of formats. Flow-through element can be used in conventional filter structures including cartridge panel in some other filter structures, with the element in a pleated or unpleated mode. Similarly, the flow-by media can be included in the panel and cartridge structures.

One preferred mode of use of the flow-by material is in a rolled media. Rolled media are prepared by first forming the fine fiber and particulate layer by heat treating the fiber layer if needed and then rolling the element into a multi-layered roll having anywhere from 2 to 50 layers. The thickness of the roll, or a separation between the layers, determines the flow rate of fluid through the structure. The flow rates can be improved by introducing channels into the rolled media. Such channels can be preformed in the substrate upon which the fine fiber is spun, or the channels can be formed into the element after the fine fiber layer is formed on the substrate and then heat treated if necessary. Mechanical forms or spacers can be included with the processing steps. The forms or spacers can introduce the channel into the structure. At least one spacer portion can be included with the rolled material to inherently form a channel in one portion of the rolled structure. Further, additional spacers can be placed such that each layer of the rolled structure has at least one channel portion. An arbitrary number of spacers can be used. At least one spacer per layer can be used up to 5, 10 or 20 spacers per layer. After the spacer layers form a channel in the element, the spacers can be removed. The spacers can be removed in one mode by unrolling the element and physically removing the spacers from the element. However, in another mode, the spacers can be simply washed from the rolled assembly using a solvent in which the spacer (but not the substrate fine fiber or particulate) is soluble, thus removing the spacers and leaving flow-through channel structures. The spacers can be configured in virtually any shape or structure as long as the spacer can provide a channel from the first end of the roll to the second end of the roll providing a flow through path for fluid. Preferably the dimensions of the channel are greater than about 1 mm in major dimension and can range from about 1 to 500 mm in major dimension. The profile of the channels can be round, oval, circular, rectangular, square, triangular, or other cross-sectional profile. The profile can be regular, or it can be irregular and amorphous. Further along the channel, the cross-sectional profile of the channel can vary from one end to the other. For example, at the intake end of the rolled structure, the channel can have a relatively large cross-sectional area, whereas at the opposite end the cross-sectional area can be smaller than the input end. Additionally the input end can be smaller in cross-sectional area than the output end. Any other variation in size of the spacer can increase turbulence in the flow resulting in improved contact between the fluid and the particulate.

The active web or element of the invention can contain the fine fiber layer with the particulate dispersed within the fiber layer to absorb/adsorb or react with materials entrained in the mobile fluid phase. Such an element or web can be combined with other active or reactive species in a variety of forms. The particulate of the invention can be discrete particles separate from the fiber or the particulate can be adhered to or on the surface of the fiber. Where the particulate is a bioactive species, it can be combined with the element or fiber web either by inoculation into the fiber web, or by dispersion of the bioactive particulate in the fiber web, as described below. The particulate can be embedded into the fiber and can be partially or fully surrounded by the fiber mass. In order to form these structures, the particulate can be combined with the fiber after spinning, can be added to the fiber during spinning in the time the fiber dries and solidifies, or can be added to the spinning solution before spinning such that the particulate is embedded partially or fully in the fiber.

One method of forming an active layer can be by dispersing the active particulate in an aqueous or non-aqueous phase containing components that can either form the active or bioactive particulate into a sheet layer or adhere the active particulates to one or more of the components of the web or element of the invention. Any of the active particulates of the invention can be incorporated into either an aqueous or non-aqueous liquid phase for such purposes. In forming the non-aqueous material, a non-aqueous solvent, preferably a volatile solvent including such materials as lower alcohols, ethers, low boiling hydrocarbon fractions, chloroform methylene chloride, dimethyl sulfoxide (DMSO) and others, can be prepared by incorporating the active particulate of the material with soluble or dispersible binding materials. Such a solution can be applied to a fiber particulate sheet like substrate or other materials to form a layer containing the active particulates that can act in that form to absorb/adsorb or react with materials entrained in the mobile fluid phase. Alternatively, the active particulate of the invention can be dispersed in an aqueous solution or suspension of binding materials that can be similarly combined with, or coated on, fiber particulate or web sheet like substrates to form an active layer of active particulate. Alternatively, the active particulate of the invention can be dispersed or suspended in a mixed aqueous organic phase that combines an aqueous phase with organic phase. The organic phase can comprise additional solvents or other organic liquids or can comprise aqueous polymeric phase such as acrylic polymers, PTFE polymers. Such mixed phases can form layers containing the active particulate and additionally can contain cross-linking components that can form bonds between adjacent polymers, further curing the coatings of films.

A heat treatment or thermal bonding process can be used to form a distinct layer in which there is no fully distinct fiber. The heat treatment can heat the individual fibers to a temperature at or above a fusion or melting point of the individual fibers and then cause the fibers to adhere, coalesce, or form into a fused network, membrane or membrane-like structure. Depending on the temperature and pressure and time of the heat treatment, the heat treatment can convert the fibers from a randomly distributed layer of fiber of intermediate length having only surface contact into a layer where fibers are more intimately associated. At a minimum, the fiber is heated such that at the intersections of the fibers, the fibers fuse to form a fused network. With additional heat pressure, or time of heat treatment, the fibers can further melt and further coalesce into a more intimately associated web. With further temperature, time, and pressure, the fiber can more fully melt and spread into a porous membrane-like structure. The heat treatment also can alter the location of the particulate. In the instance that the fiber is simply distributed throughout, the particulate is distributed through the fine fiber. The heat treatment can fix the particulate into a structure in which the particulate is surface bonded to the heat treated fibrous, web, or membrane-like structure, however, depending again, on the temperature, time of heating, and pressure, the particulate can be incorporated into and throughout the porous membrane-like structure. Such a heat treated or calendared structure can have a layer of thickness that approximates that of the original fine fiber layer, or results in a layer that is thinner than the original fine fiber layer. Accordingly, if the original fine fiber layer has a thickness that ranges from about 0.5 to 200 microns, the resulting layer can have a thickness that ranges from about 0.5 to about 150 microns or smaller often up to 100 microns and sometimes up to 50 microns, depending on the amount of fiber spun, the particulate content and the degree of heat treatment, including heating, pressure, and time. One form of such a heat treatment process is the calendaring operation that can be used thermally. The calendaring process uses rollers, rollers and embossers, or embossers to form the heat treated layers. An embosser can be used with a bonding pattern that can result in a regular, intermediate, or random pattern. When a pattern is used, the pattern can occupy up to 50 percent of the surface area or more. Typically, the bonded array occupies about 1 to 75 percent of the surface area, often about 10-50 percent of the surface area.

Depending on the nature of the fine fiber used in the various layers and the rate of manufacture of the composites, the calendaring process parameters such as time, temperature, and pressure can be varied to achieve acceptable results. The temperature of the calendared rollers can range from about 25-200° C. The pressure exerted on the layers using the calendaring rollers or combination of rollers can range up to 500 psi and the speed of the composite through the heat treatment station can range from about 1 to about 500 feet per minute. The operating parameters of the heat treatment station must be adjusted such that the appropriate amount of heat is delivered to the fiber to obtain the correct ultimate structure. The heat cannot be so little as not to soften or melt some portion of the fiber and cannot be such that the fiber is simply melted and dispersed into the substrate. The total heat delivered can be readily adjusted to bond the fiber, soften the fiber overall or fully form the fibers into a porous membrane. Such minor adjustment of the operating parameters is well within the skill of the artisan.

The web or element of the invention can be comprised of a variety of different layers. Such layers can include both active and inactive layers. Active layers typically comprise a web of fine fiber with the particulates dispersed within the fine fiber or other impregnated layers or layers containing adsorbent/absorbent or reactive particulate or other such structures. Such layers can be formed into the useful element of the invention combined with protective layers, spatial layers, active layers, inactive layers, support layers, and all can be incorporated or encapsulated into conventional cartridge panel or other such protective structures. A preferred form of the active particulate comprises an adsorbent carbon particulate.

For filter applications in particular, the fine fiber layers formed on the substrate in the filters of the invention should be substantially uniform in particulate distribution, filtering performance and fiber distribution. By substantial uniformity, we mean that the fiber has sufficient coverage of the substrate to have at least some measurable filtration efficiency throughout the covered substrate. The media of the invention can be used in laminates with multiple webs in a filter structure. The media of the invention includes at least one web of a fine fiber structure. The substrate upon which the fine fiber and active particulate can be formed can be either active or inactive substrate. Such substrates can have incorporated into the substrate layer active materials in the form of coatings, particulates, or fibers that can add adsorbent/absorbent or reactive properties to the overall structure.

In an embodiment, the overall thickness of the fiber web is about 1 to 100 times the fiber diameter or about 1 to 300 micron or about 5 to 200 microns. The web can comprise about 5 to 95 wt.-% fiber and about 95 to 5 wt.-% active particulate or about 30 to 75 wt.-% fiber and about 70 to 25 wt.-% active particulate occupies about 0.1 to 50 vol % of the layer or about 1 to 50 vol % or 2 to 50 vol % of the layer. The overall solidity (including the contribution of the active or inactive particulate) of the media is about 70% or less, or 0.1 to about 50%, preferably about 1 to about 30%. The solidity of the web without including the contribution of the particulate in the structure is about 10 to about 80%. The filter media of the invention can attain a filtration efficiency of about 40 to about 99.99% when measured according to ASTM-1215-89, with 0.78µ monodisperse polystyrene spherical particles, at 13.21 fpm (4 meters/min) as described herein. The filtration web of the invention typically exhibits a Frazier permeability test that would exhibit a permeability of at least about 1 meters-minutes$^{-1}$, preferably about 5 to about 50 meters-minutes$^{-1}$ When used as a inactive particulate or separation means, the particulate that characterizes the particulate phase of the web of the invention is a particulate that is either inert to the mobile phase and the entrained contaminant load or has some defined activity with respect to the mobile fluid or the load.

The particulate materials of the invention have dimensions capable of improving both the filtration properties of the media and the active reactive, absorbent or adsorbent character of the structures of the invention. The materials can be made of a variety of useful materials. The materials can either be substantially inert to the mobile phase and entrained particulate load passing through the web or the materials can interact with the fluid or particulate loading. In an "inert" mode, the spacer particulate simply alters the physical parameters of the fiber layer and the media including one or more fiber layers. When using a particulate that interacts with the fluid or the particulate loading, the particulate can, in addition to altering the physical properties of the media or layers, react with or absorb or adsorb a portion of either the mobile fluid or the particulate loading for the purpose of altering the material that passes through the web. The primary focus of the technology disclosed herein is to improve the physical structure and absorptive, reactive or adsorptive character of the media or layers and to improve filter performance. For that purpose, an active or an inert particle can be used. In certain applications, a substantially inert particle can be used in combination with a particulate that interacts with the mobile phase or particulate loading. In such applications, a combination of an inert particle and an interactive particle will be used. Such a combination of active particulate and inert particulate can provide both improved filter property and absorption, or adsorption properties.

The preferred bioactive, adsorptive or absorptive means comprises a particulate. Such a particulate, used in a fibrous structure of the invention, occupies space within the multilamellar stack or matrix, reduces the effective density of the fiber, increases the tortuous pathways of the fluid through the filter and absorbs, adsorbs or reacts with the fluid or materials dissolved or dispersed in the fluid. Alternatively, the particulate can provide the mechanical space holding effect while additionally chemically reacting with the mobile fluid or adsorbing or absorbing gaseous, liquid or solid components that are biological impurities or contaminates in the mobile fluid. The active layer of the invention can comprise a nanofiber layer and dispersed within the nanofiber layer, the bioactive, absorptive, or adsorptive particulate of the invention. In an embodiment, the nanofiber layers of the invention range from about 25 nm to 2.0 microns, 0.5 to about 300 microns, 1 to about 250 microns or 2 to about 200 microns in thickness and contain within the layer about 0.1 to about 50 or 10 to about 50 vol % of the layer in the form of both inert (if any) and the active particulate of the invention. In this case, the bioactive particulate of the invention can be combined with inert spacer particulate in some amount. The bioactive particulate of the invention acting to absorb, adsorb or react with contaminants within the fluid flow while the inert particulate simply provides an excluded volume within the layer to reduce solidity, improve efficiency and other filtration properties.

The creation of low pressure drop active particulate, chemically reactive, absorptive, or adsorptive substrates for the removal of gas phase contaminants from airstreams is from flat sheet rolls of absorptive/adsorptive/reactive media that are layered or rolled together with a spacer media to form an adsorptive/reactive substrate with open channels and absorptive/adsorptive/bioactive walls. Additionally, the spacer media can be made to be absorptive/adsorptive/bioactive so as to contribute to the overall life/performance of the final chemical unit. The spacer media that creates the open channels can be created from a mesh, single lines of a polymer bead, glue dots, metal ribs, corrugated wire/polymer/paper mesh, corrugated metal/paper/polymer sheets, strips of polymer, strips of adhesive, strips of metal, strips of ceramic, strips of paper, or even from dimples placed in the media surface. These spacer media can be made absorptive/adsorptive/bioactive by coating them or extruding/forming them with/from absorptive/adsorptive/bioactive materials. The channel size and shape is controlled by the shape and size of the space media. Examples include squares, rectangles, triangles, and obscure shapes that may be created by a dotted pattern of polymer/adhesive. The chemistry of the walls and spacer media can be made specific to adsorb acidic, basic, and organic and water vapors, as well as several specific classes of compounds including reactive carbonyl compounds, including formaldehyde, acetaldehyde and acetone, and harmful biological products or contaminates.

The combination of particles and fibers (also nanofibers) results in a material that offers several advantages: increased diffusion; allowing for the use of smaller particles, thereby increasing the external surface area and hence the reaction rate; increased permeation into the reactive layer; the combination of particle and chemical filtration into a single layer; and the direct application of reactants to a filtration application without the need of a substrate or carrier (i.e. impregnated adsorbent).

Besides using particles that have been inoculated or adhered to a reactive or bioactive species, it should be obvious to anyone skilled in the art that these modifications to particulates can be performed after forming the fibrous web and structures. Imparting reactive activity to the particles and web after forming the fibrous web and structure can be accomplished using many different coating processes. For example, spray coating, dip coating, aerosol deposition, chemical vapor deposition, Kiss coating, and vacuum coating. A final step may involve a drying process that may, or may not, include thermal treatments, gas purging, or vacuum methods.

In an embodiment an active and/or bioactive particulate is deposited onto a substrate that can be any thin, flexible, porous substrate (e.g. a scrim, paper, mesh, etc.). The nanofibers bind the active bioactive particulate in a thin layer and, as such, minimize the shedding of particles. This entire combination of substrate layer and nanofiber/bioactive layer is then rolled with a spacer layer that provides non-restrictive channels for fluid flow or transport. The layer can comprise a mix of particulates that each react with a different chemical species. For example, the active or bioactive particulate may be specific for acidic, basic, or reactive organic contaminants. Examples active particulates include citric acid for the removal of amines and ammonia; potassium hydroxide for the removal of sulfur dioxide and other acid gases; and 2,4-dinitrophenylhydrazine for the removal of carbonyl containing compounds. Another aspect of the invention is the use of nanofibers and citric acid powder, or granules, inoculated or deposited onto a substrate that can be any thin, flexible, porous substrate (e.g. a scrim, paper, mesh, etc.).

The nanofiber binds the bioactive particles in a thin layer, and as such, minimizes the shedding of particles. This entire combination of substrate layer and nanofiber/bioactive layer is then rolled with a spacer layer that provides non-restrictive channels for fluid flow or transport.

A media construction according to the present invention includes a first layer of fibrous media or substrate having a first surface. Preferably the first layer of permeable coarse fibrous material comprises fibers having an average diameter of at least 10 microns, typically and preferably about 12 (or 14) to 30 microns. Also preferably the first layer of fibrous material comprises a media having a basis weight of no greater than about 200 grams/meter$^2$, preferably about 0.50 to 150 g/m$^2$, and most preferably at least 8 g/m$^2$. Preferably the first layer of fibrous media is at least 0.0005 inch (12 microns) thick, and typically and preferably is about 0.001 to 0.030 inch (25-800 microns) thick. The element of the invention, including the fine fiber and dispersed particulate layer can be combined with a variety of other layers as discussed elsewhere in the specification. The layers can be made as a flat or coplanar sheet version of the layers of the invention or can be pleated, corrugated or formed into virtually any other cross-sectional shape needed to form the low pressure drop flow through element of the invention. The substrate can comprise an expanded poly PTFE layer or Teflon layer. The substrate can also be substantially free of a Teflon, an expanded poly PTFE layer, or stretched PTFE fiber or layer. Such layers are useful in a variety of in use applications that can provide both filtration and activity from the active particulate. Such layers can also aid in confining the particulate into the element.

In preferred arrangements, the first layer of fibrous material comprises a material which, if evaluated separately from a remainder of the construction by the Frazier permeability test, would exhibit a permeability of at least 1 meter(s)/min, and typically and preferably about 2-900 meters/min. Herein when reference is made to efficiency, unless otherwise specified, reference is made to efficiency when measured according to ASTM-1215-89, with 0.78µ monodisperse polystyrene spherical particles, at 20 fpm (6.1 meters/min) as described herein.

Preferably the layer of fine fiber material secured to the first surface of the layer of permeable coarse fibrous media is a layer of nano- and microfiber media wherein the fibers have average fiber diameters of no greater than about 2 microns, generally and preferably no greater than about 1 micron, and typically and preferably have fiber diameters smaller than 0.5 micron and within the range of about 0.05 to 0.5 micron. Also, preferably the first layer of fine fiber material secured to the first surface of the first layer of permeable coarse fibrous material has an overall thickness that is no greater than about 30 microns, more preferably no more than 20 microns, most preferably no greater than about 10 microns, and typically and preferably that is within a thickness of about 1-8 times (and more preferably no more than 5 times) the fine fiber average diameter of the layer.

The element of the invention when used in a filtration mode should have a minimal pressure drop for acceptable function as a filter and to obtain the activity of the active particle(s). Such pressure drop information is known for the types of filtration devices of the invention. Such pressure drop parameters define the useful life of the filtration element of the invention. The element of the invention, when used in a flow through mode with no intervening filter layer, should provide little or no resistance to the flow of the mobile fluid through the element (e.g.; less 0.1 inches or less than 1-5 inches of water). Flow should not be constrained but the residence time, however, of the fluid within the element must be sufficient to obtain sufficient contact and absorbance/adsorbance/reaction needed in the element to obtain the desired activity form the active particulate within the element. A useful residence time, depending on active particulate can be from about 0.01 to as long as it is necessary to obtain some removal of entrained materials. The residence time can be 0.02 second to as much as 5 minutes and typically ranges from about 0.01 to 60 seconds 0.01 to 1 second or as little as 0.02 to 0.5 second. The lifetime of such a unit is defined by the load of active particulate and the residual amount of activity in the unit. Some small amount of pressure drop can be designed into the element to slow the flow and extend residence time without substantially impeding flow.

The media, web, layers or elements of the invention can be regenerated. In the case of a reactive particulate in the invention, the particulate can be regenerated by chemically treating the particulate. In the case of absorptive or adsorptive particulate, the particulate can be generated by heating the element to a temperature sufficient to drive the absorbed or adsorbed material from the particulate surface or internal structure. The element can also be evacuated such that the effects of reduced pressure can remove the volatile material from the surface of the adsorptive particle or from the interior of the absorptive particle.

The reactive species can be regenerated by first removing any reaction byproducts from the reaction from the active species with the entering material in the fluid phase. In one such reaction, byproducts are removed, the particulate remaining within the element enhanced by passing a solution or suspension of the active material through the element, causing the interior structure including the fine fiber layer to accumulate additional amounts of reactive material.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method of converting cellulosic biomass to ethanol or butanol, comprising:
   a) culturing a microorganism on a growth media comprising a substrate and two or more substantially continuous synthetic, electroprocessed fine fiber network layered to form a multi-lamellar matrix wherein ethanol or butanol is a metabolic product of fermentation by the microorganism, each fiber layer comprising a thickness of about 25 nm to about 2000 nm, a solidity of 70% or less, fibers comprising a non-cytotoxic polymer, and fiber diameter of about 10 nm to about 1000 nm, wherein one or more of the fiber layer include fibers comprising cellulose or a particulate comprising cellulose dispersed within the fiber layer; and
   b) contacting the cultured growth media under conditions that promote microbial fermentation with cellulosic biomass or with pentose or hexose sugars obtained from conversion of the cellulosic biomass to pentose or hexose sugars.

2. The method of claim 1, wherein the polymer is polyester or polyamide.

3. The method of claim 1, wherein the polymer is poly epsilon caprolactone, polyglycolate, polylactate, or nylon.

4. The method of claim 1, wherein the growth media further comprises an enzyme, bioactive molecule, or mixture thereof.

5. The method of claim 1, wherein the microorganism comprises a cellulose binding domain (CBD).

6. The method of claim 1, wherein one or more of the fiber layers of the growth media comprises an active particulate, an inert particulate, or mixtures thereof.

7. The method of claim 1, wherein one or more of the fiber layers of the growth media comprises an absorbent particulate, an adsorbent particulate, a reactive particulate, or a mixture thereof.

8. The method of claim 1, wherein the layer comprises about 5 to 95 wt % fiber and about 95 to 5 wt % particulate comprising an active particulate, inert particulate, or mixture thereof.

9. The method of claim 1, wherein the layer comprises about 30 to 75 wt % fiber and about 70 to 25 wt % active particulate.

10. The method of claim 1, further comprising:
converting cellulosic biomass to pentose or hexose sugars, wherein said converting comprises contacting a growth surface comprising a substrate and two or more substantially continuous fine fiber network layered to form a multi-lamellar matrix with cellulosic biomass, each fiber layer comprising a thickness of about 25 nm to about 2000 nm, a solidity of 70% or less, a bioactive particulate dispersed in the fiber layer, and the fiber comprises a diameter of about 10 nm to about 1000 nm, wherein the bioactive particulate of the growth surface comprises a cellulase or cellulosome capable of converting cellulose, pectin, starch, xylan, or a mixture thereof to pentose or hexose sugars; and contacting the cultured growth media in step a) with the pentose or hexose sugars under conditions that promote microbial fermentation, wherein ethanol is a metabolic product of the fermentation.

11. The method of claim 1, wherein the microorganism is capable of fermenting cellulose, pectin, starch, xylan, or a mixture thereof.

12. The method of claim 1, wherein the microorganism comprises a *Clostridium* species or *Saccharomyces* species.

13. The method of claim 12, wherein the microorganism comprises *Clostridium phytofermentans*, or *Saccharomyces serevisae*.

14. The method of claim 1 wherein the cellulose comprises cellulose esters, xylan, pectin, chitin, methyl cellulose, ethyl cellulose, hydroxymethyl cellulose, or hydroxyethyl cellulose.

15. The method of claim 1, wherein the substrate comprises a cellulosic substrate.

16. The method of claim 15, wherein the substrate comprises cellulosic fibers.

17. The method of claim 16, wherein the substrate further comprises non-cellulosic stabilizing fibers.

* * * * *